(12) United States Patent
Descamps et al.

(10) Patent No.: US 8,735,624 B2
(45) Date of Patent: May 27, 2014

(54) POLYMORPHIC FORM OF CHDMAPP, METHOD OF PREPARATION THEREOF, AND PHARMACEUTICAL COMPOSITION COMPRISING SAME

(75) Inventors: Guillaume Descamps, Rouen (FR);
Youness Amharar, Rouen (FR);
Yohann Cartigny, Bois Guillaume (FR);
Gérard Coquerel, Boos (FR)

(73) Assignee: Innate Pharma, Marseilles (FR)

( * ) Notice: Subject to any disclaimer, the term of this patent is extended or adjusted under 35 U.S.C. 154(b) by 443 days.

(21) Appl. No.: 13/063,248

(22) PCT Filed: Sep. 8, 2009

(86) PCT No.: PCT/EP2009/061607
§ 371 (c)(1),
(2), (4) Date: May 11, 2011

(87) PCT Pub. No.: WO2010/029062
PCT Pub. Date: Mar. 18, 2010

(65) Prior Publication Data
US 2011/0245534 A1    Oct. 6, 2011

Related U.S. Application Data

(60) Provisional application No. 61/095,746, filed on Sep. 10, 2008.

(51) Int. Cl.
*C07F 9/28*    (2006.01)
(52) U.S. Cl.
USPC .......................................................... 562/22
(58) Field of Classification Search
USPC .......................................................... 562/22
See application file for complete search history.

(56) References Cited

FOREIGN PATENT DOCUMENTS

WO    WO 03/009855    2/2003
WO    WO 2007039635 A2 *    4/2007

OTHER PUBLICATIONS

Descamps, G. "Purification by Crystallization of a New Organo-Phosporous Active Principle That Modulates Tγ9δ2 Lymphocyte Activity", pp. 1-3 (pp. 81-82 of the thesis), unpublished Doctoral Thesis.
Aubin, E. "Purification by Crystallization of a New Organo-Phosporous Active Principles, and Study of the Preferential Crystallization of Ethanolamine Mandelate", pp. 1-3 (pp. 65-66 of the thesis), unpublished Doctoral Thesis.
Examination Report in EPO Application No. 09 782 743.0, dated Dec. 21, 2011, pp. 1-4.
Reply to Examination Report in EPO Application No. 09 782 743.0, dated Jun. 29, 2012, pp. 1-3.
Decision to Grant in EPO Application No. 09 782 743.0, dated Dec. 5, 2013, pp. 1-2.
Complete file history for EPO Application No. 09 782 743.0, downloaded Dec. 26, 2013, pp. 1-261.
Descamps. G. et al., "Structural and physicochemical Characterization of a Solid Solution Produced by Antisolvent Crystallization of a New Phosphoantigen" *Crystal Growth and Design*, Aug. 5, 2009, pp. 3910-3917, vol. 9, No. 9.

* cited by examiner

*Primary Examiner* — Johann R Richter
*Assistant Examiner* — Kofi Adzamli
(74) *Attorney, Agent, or Firm* — Saliwanchik, Lloyd & Eisenschenk

(57) ABSTRACT

The present invention relates to novel polymorphs of (2E)-1-hydroxy-2-methylpent-2-enyl-pyrophosphonate disodium (CHDMAPP-$Na_2$), to the process for preparing them and to the pharmaceutical compositions containing them.

17 Claims, 14 Drawing Sheets

|   | x | Y | z | U(eq) |
|---|---|---|---|---|
| Na(1) | 5555(1) | -3370(1) | -2140(1) | 27(1) |
| Na(2) | 14232(1) | -3857(1) | 4413(1) | 25(1) |
| OW | 4470(2) | -3273(2) | -99(2) | 29(1) |
| P(1) | 3556(1) | -5324(1) | -2614(1) | 17(1) |
| P(2) | 7147(1) | -1662(1) | 36(1) | 18(1) |
| O(1) | 4496(1) | -6208(1) | -2494(2) | 24(1) |
| O(2) | 2987(1) | -5174(1) | -1187(2) | 24(1) |
| O(3) | 6985(1) | -2963(1) | -397(2) | 25(1) |
| O(4) | 7405(1) | -919(1) | -1378(2) | 21(1) |
| O(5) | 6214(1) | -1047(1) | 720(2) | 24(1) |
| O(6) | 3822(1) | -4098(1) | -3169(2) | 24(1) |
| O(7) | 12900(1) | -3111(2) | 2671(2) | 35(1) |
| C(1) | 8389(2) | -1499(2) | 1096(2) | 30(1) |
| C(2) | 9445(2) | -1826(3) | 395(3) | 48(1) |
| C(3) | 10400(2) | -1871(3) | 1466(3) | 40(1) |
| C(4) | 10981(2) | -2834(2) | 1851(3) | 32(1) |
| C(5) | 11832(2) | -2759(2) | 3052(3) | 33(1) |
| C(6) | 10850(3) | -4063(3) | 1177(3) | 59(1) |
| HW1 | 4790(2) | -3430(3) | 690(3) | 40 |
| HW2 | 3970(3) | -3660(3) | -160(3) | 40 |
| H2 | 2979 | -5829 | -778 | 40 |
| H7 | 13185 | -2552 | 2253 | 40 |
| H1A | 8444 | -664 | 1410 | 40 |
| H1B | 8337 | -2002 | 1928 | 40 |
| H2A | 9361 | -2609 | -62 | 40 |
| H2B | 9589 | -1228 | -322 | 40 |
| H3 | 10600 | -1142 | 1900 | 40 |
| H5A | 11863 | -1932 | 3401 | 40 |
| H5B | 11610 | -3275 | 3814 | 40 |
| H6A | 10373 | -4552 | 1715 | 40 |
| H6B | 11555 | -4447 | 1151 | 40 |
| H6C | 10539 | -3973 | 233 | 40 |

FIG. 10

|      | U11    | U22   | U33   | U23   | U13    | U12    |
|------|--------|-------|-------|-------|--------|--------|
| Na(1)| 29(1)  | 30(1) | 23(1) | -4(1) | 2(1)   | -6(1)  |
| Na(2)| 27(1)  | 25(1) | 24(1) | 3(1)  | 2(1)   | 1(1)   |
| OW   | 31(1)  | 32(1) | 22(1) | 2(1)  | -5(1)  | -7(1)  |
| P(1) | 18(1)  | 18(1) | 15(1) | -1(1) | 1(1)   | -1(1)  |
| P(2) | 18(1)  | 20(1) | 18(1) | 2(1)  | -1(1)  | 1(1)   |
| O(1) | 22(1)  | 30(1) | 21(1) | 0(1)  | -1(1)  | 5(1)   |
| O(2) | 35(1)  | 18(1) | 20(1) | 0(1)  | 7(1)   | 1(1)   |
| O(3) | 31(1)  | 20(1) | 23(1) | 3(1)  | 0(1)   | -1(1)  |
| O(4) | 17(1)  | 26(1) | 22(1) | 6(1)  | 1(1)   | 2(1)   |
| O(5) | 24(1)  | 27(1) | 22(1) | 2(1)  | 3(1)   | 3(1)   |
| O(6) | 28(1)  | 21(1) | 22(1) | 1(1)  | 2(1)   | -5(1)  |
| O(7) | 24(1)  | 38(1) | 44(1) | 10(1) | -2(1)  | 1(1)   |
| C(1) | 24(1)  | 38(1) | 27(1) | -3(1) | -7(1)  | 4(1)   |
| C(2) | 27(1)  | 81(2) | 37(2) | -2(1) | -7(1)  | 9(1)   |
| C(3) | 24(1)  | 55(2) | 40(2) | -8(1) | -6(1)  | 4(1)   |
| C(4) | 22(1)  | 43(1) | 30(1) | -1(1) | -2(1)  | -6(1)  |
| C(5) | 25(1)  | 44(1) | 31(1) | 0(1)  | -4(1)  | -1(1)  |
| C(6) | 72(2)  | 47(2) | 55(2) | 4(1)  | -25(2) | -16(2) |

US 8,735,624 B2

POLYMORPHIC FORM OF CHDMAPP, METHOD OF PREPARATION THEREOF, AND PHARMACEUTICAL COMPOSITION COMPRISING SAME

CROSS-REFERENCE TO RELATED APPLICATION

This application is the U.S. national stage application of International Patent Application No. PCT/EP2009/061607, filed Sep. 8, 2009, which claims the benefit of U.S. Provisional Patent Application No. 61/095,746, filed Sep. 10, 2008, the disclosures of which are hereby incorporated by reference in their entireties, including all figures, tables and amino acid or nucleic acid sequences.

FIELD OF THE INVENTION

The present invention relates to a novel polymorphic forms of (2E)-1-hydroxy-2-methylpent-2-enyl-pyrophosphonate disodium (CHDMAPP-$Na_2$) compounds, to method for making them, to pharmaceutical compositions containing them and to the use in therapy.

BACKGROUND OF THE INVENTION

When crystallized, a given molecule may give rise to a variety of polymorphs and solvates each presenting distinct crystal structures and physical properties like solubility, melting points, desolvation temperatures, X-ray diffraction patterns, solid state NMR spectra, apparent and true densities, crystal friability, powder flowability, and/or powder compressibility.

As a result, a change in the crystalline form of a given drug may affect the safety and efficacy of the drug product (Knapman et al, K. Modern Drug Discoveries, March 2000:53). For example, many antibiotics, antibacterials, tranquilizers, etc., exhibit polymorphism and the polymorphic forms of a given drug may exhibit superior bioavailability and therefore have higher activity compared to other polymorphs. It is therefore crucial, upon the development of a novel therapeutic drug, to determine which polymorphic form or solvate is the most suited for the administration to a subject.

Phosphoantigens comprises a large group of phosphate-containing compounds that activate γδ T cells (Fournié et al, Res. Immunol., 1996, 147(5), 338-347, Belmant et al, FASEB, 2000, 14(12), 1669-1670, Espinosa et al, Microbes and Infections, 2001). CHDMAPP and related organo-phosphorous compounds, and their method of preparation and their therapeutic use, have been disclosed in U.S. Pat. No. 7,399,756. These organo-phosphorous compounds are useful in the activation of γδ T cells and are therefore promising agents for the treatment and prevention of cancer, infectious diseases and auto-immune diseases. One compound in particular, CHDMAPP, also named (2E)-1-hydroxy-2-methylpent-2-enyl-pyrophosphonate, (Boëdec A. et al, J Med. Chem. 2008 Mar. 27; 51(6):1747-54) has been proven to be a very potent activator of γδ T cells. Its in vitro activity is approximately 100 times higher than that of another known highly active γδ T cell compound BrHPP (Phosphostim™).

Traditional preparation of CHDMAPP is made in a convergent manner, in four steps according to publications from Hecht et al. (Hecht et al., *Tetrahedron Letters*, 43 (2002) 8929-8933) for the preparation of (E)-4-chloro-2-methylbut-2-en-1-ol, Miyashita et al. (Miyashita et al., *J. Org. Chem.* 42 (1977) 3772-3774) for the preparation of (E)-4-chloro-2-methylbut-2-en-1-(pyranyl-2'-oxy), this intermediate compound is coupled with a phosphonylating agent (obtained according to Valentijn et al., *Synlett* (1991) 663-664 and demethylated as reported by Phan and Poulter (J. Org. Chem. (2001), 66, 6705-6710)) to obtain the pyranyl-2'-oxy derivative.

Recent development have shown that phosphoantigens can form salts with selected organic bases, e.g. benzathine, to obtain a highly pure product in crystalline form, as disclosed in PCT publication no. WO 07/039,635. However, the solubility of theses salts in water is sometimes poor, which does not favour bioavailability (BCS class 2 or 4). Interestingly, only organic salts were found to be suitable for preparing pure crystalline phosphoantigens (such as the weak agonist IPP). BrHPP (commonly named Phosphostim™) does not appear to yield a stable crystalline form with a mineral base.

Because sodium is particularly well suited for pharmaceutical use, the organic salt of CHDMAPP is typically processed on an ion exchange resin to obtain CHDMAPP sodium salt as a solution in water. The obtained solution can be concentrated; ultimately, in certain cases the compound may be crystallized. This crystallisation step, conducted in standard conditions, leads to either a hygroscopic anhydrous solid compound or to a heterogeneous mixture of ill defined solid phases, the crystallisation of one form or the other being particularly hard to control. However, the obtained compound is not homogenous and may greatly vary upon two successive crystallisation steps. CHDMAPP can also be stored in liquid form. However, solid forms are in many cases preferable to liquid compositions for pharmaceutical purposes.

There remains therefore a need for novel phosphoantigen compound that is well characterized, in a homogenous solid form, presenting a very high stability, having improved processing properties, being water soluble and safe for direct administration to a patient.

SUMMARY

The present invention is based on the selective crystallization of a novel monohydrate form of CHDMAPP disodium salt (CHDMAPP-$Na_2$,$1H_2O$). This novel crystalline form presents many advantages, such as improved stability of the active compound, very low hygroscopicity of the bulk drug product powder, high chemical and structural purity, ease of powder handling and high water solubility, thereby improving its processing properties, its storage, its sampling, and its administration to the patient.

The present invention also provides a controlled, high yield, industrial scale, manageable process for crystallisation of CHDMAPP disodium monohydrate salt.

CHDMAPP monohydrate preferably exists as a crystallized solid. This pure solid phase constitutes a powder, having improved properties compared to other solvates or polymorphic forms of the sodium salt.

For the above mentioned reasons, any modification of the solid state of a drug substance for oral administration in the form of a more stable and pure product is expected to provide a consistent advantage over less stable forms of the same drug.

The present invention provides a substantially pure CHDMAPP composition in crystalline form. In an aspect of the invention, the CHDMAPP crystalline form is the crystallisation product of a CHDMAPP and a mineral base. In another aspect, said mineral base is sodium. In a preferred aspect, sodium is present as 2 atoms per CHDMAPP molecule. The present invention provides a crystalline of (2E)-1-hydroxy- 2-methylpent-2-enyl-pyrophosphonate disodium composition (CHDMAPP-Na$_2$), in one embodiment, said composition is a monohydrate polymorph (CHDMAPP-Na$_2$,1H$_2$O), in another embodiment, said composition is an anhydrous polymorph (CHDMAPP-Na$_2$,0H$_2$O).

The monohydrate polymorph (CHDMAPP-Na$_2$,1H$_2$O) can be characterized by the following parameters individually or in any combination or two, three, four or more, or all of, such parameters: the XRPD pattern; stabilization property at temperatures up to 115° C.±2° C.; a DSC pattern which comprises an endothermic peak having an onset temperature of about 115° C.±2° C. and a maximum peak temperature of about 130° C.±2° C.; a DSC pattern substantially the same as the pattern of FIG. 7; TGA pattern, which comprises a loss of mass of approximately 5%±2% at 115° C.±2° C.; the TGA pattern of FIG. 7; a DVS pattern wherein no substantial weight gain occurs before about 80%±2% RH, in particular wherein the weight of composition does not vary by more than 5% at 80% relative humidity when the composition is analyzed over a relative humidity range from 0 to 90% in 3 steps and where each step is brought to equilibrium before moving to next step, with equilibrium assessed as a weight change of less than 0.002 mg (0.02%) for five consecutive points at 1 point per 120 seconds; the DVS pattern of FIG. 6, its crystallographic parameters as depicted in table 5 below.

The anhydrous polymorph (CHDMAPP-Na$_2$,0H$_2$O) can be characterized by one or more parameters selected from the group consisting of: the XRPD pattern depicted in FIG. 3, the crystallographic parameters depicted in Table 2 below, and the DVS pattern as described in FIG. 5.

The present invention provides CHDMAPP crystallized as a monohydrate.

In an embodiment, the crystalline form of CHDMAPP monohydrate is characterized by an XRPD pattern comprising at least one of the peaks (2-theta angles) selected from the group consisting of the peaks at about: 7.25; 10.81; 12.32; 14.04; 14.54; 16.06; 16.61; 17.61; 18.68; 19.44; 19.80; 20.13; 21.34; 21.84; 23.36; 24.52; 25.26; 25.98; 26.84; and 27.16. In a preferred aspect, the crystalline form of CHDMAPP monohydrate is characterised by an XRPD pattern comprising at least four, at least five, at least six of the above listed peaks.

The present invention provides a crystalline form of CHDMAPP disodium monohydrate characterized by an XRPD pattern as depicted in FIG. 4.

The present invention further provides a crystalline form of anhydrous CHDMAPP characterized by an XRPD pattern comprising at least one of the peaks (2-theta angles) selected from the group consisting of the peaks at about: 6.83; 10.49; 15.04; 16.88; 17.99; 18.33; 19.12; 19.73; 19.97; 20.45; 20.86; 21.10; 22.67; 24.18; 25.95; 26.84; 27.18; 27.36; 28.90; and 29.18. In a preferred aspect, the crystalline form of anhydrous CHDMAPP is characterized by an XRPD pattern comprising at least four, at least five, at least six of the above listed peaks.

The invention provides a crystalline form of CHDMAPP that is stable until 115° C.±2° C.

The invention further provides a crystalline form of CHDMAPP characterized by a DVS pattern as described in FIG. 6.

The invention further provides a crystalline form of CHDMAPP characterized by a DSC pattern as described in FIG. 7.

The invention further provides a crystalline form of CHDMAPP characterized by a TGA pattern as described in FIG. 7.

The invention further provides a crystalline form of CHDMAPP characterized by at least one of the following crystallographic parameters:

| Chemical formula | Na$_2$[HO—CH$_2$—C(CH$_3$)=CH—(CH$_2$)$_2$—PO$_2$—O—PO$_3$H],H$_2$O |
|---|---|
| Molar mass/g · mol$^{-1}$ | 322.09 |
| Crystalline system | Monoclinic |
| Space group | P 2$_1$/c (n° 14) |
| Z | 4 |
| Z' (asymmetric unit) | 1 |
| a/Å | 12.201(1) |
| b/Å | 11.03(1) |
| c/Å | 9.495(1) |
| β (°) | 92.928(2) |
| V/Å$^3$ | 1276.1(3) |
| d$_{calc}$/g · cm$^{-3}$ | 1.677 |
| Temperature/K | RT |

Also provided is a CHDMAPP composition, particularly a CHDMAPP-Na$_2$ composition, more particularly a CHDMAPP-Na$_2$,1H$_2$O composition which is stable for a period of time of at least 3 months, at least 12 months, at ambient temperature. Also provided is a CHDMAPP composition, particularly a CHDMAPP-Na$_2$ composition, more particularly a CHDMAPP-Na$_2$,1H$_2$O composition which is substantially non-hygroscopic.

The CHDMAPP composition, particularly a CHDMAPP-Na$_2$ composition, more particularly a CHDMAPP-Na$_2$,1H$_2$O composition according to the present invention does not vary by more than 5% at 80% relative humidity when CHDMAPP is analyzed over a relative humidity range from 0 to 90% in 3 steps and where each step is brought to equilibrium before moving to next step, with equilibrium assessed as a weight change of less than 0.002 mg (0.02%) for five consecutive points at 1 point per 120 seconds.

The present invention also provides a pharmaceutical composition comprising the CHDMAPP composition, particularly a CHDMAPP-Na$_2$ composition, more particularly a CHDMAPP-Na$_2$,1H$_2$O composition. In an embodiment, the pharmaceutical composition comprises at least 50%, at least 90% by weight of the CHDMAPP composition, particularly a CHDMAPP-Na$_2$ composition, more particularly a CHDMAPP-Na$_2$,1H$_2$O composition, based upon 100% total weight of delivery agent and salts thereof in the composition. In a further aspect, said pharmaceutical composition is in the form of a tablet, or a capsule. Also envisaged are kits comprising any of the foregoing.

A unit dosage form comprising CHDMAPP composition, particularly a CHDMAPP-Na$_2$ composition, more particularly a CHDMAPP-Na$_2$,1H$_2$O composition contains between 0.5 mg and 200 g of CHDMAPP, and the CHDMAPP having purity or at least 99%. Said unit dosage form is preferably in the form of a tablet or a capsule.

The invention also provides a composition or kit comprising: CHDMAPP monohydrate in a crystalline form; and at least one second active agent. In a preferred embodiment, said second active agent is IL-2, IFNα, ribavirin or any other therapeutically active agent.

The CHDMAPP composition, particularly a CHDMAPP-Na$_2$ composition, more particularly a CHDMAPP-Na$_2$,1H$_2$O composition according to the invention is also provided in a dosage unit form further comprising an excipient, a diluent, a disintegrant, a plasticizer, a colorant, a dosing vehicle, or any combination thereof.

The present invention provides a process to obtain a solid crystalline CHDMAPP-Na$_2$,1H$_2$O composition, comprising:
1. diluting CHDMAPP-Na$_2$ in water,
2. adding an organic solvent until the formation of crystals, 3. isolating the crystals, and optionally,
4. drying the crystallized CHDMAPP-Na$_2$,1H$_2$O.

In a preferred aspect, the process comprises an optional step of seeding the medium with CHDMAPP-Na$_2$,1H$_2$O crystals. In another aspect, CHDMAPP-Na$_2$ is initially diluted in water at 25% wt. In another aspect, step (2) is be stopped when the hydro-organic solution has a composition close to 35% water/65% organic solvent. In a further aspect, the addition step (2) lasts for about at least one hour. In another aspect, step (3) takes place for a length of time of at least about 4 hours. In an aspect, in step (3) the organic solvent was added until the composition of the solution reaches 90% organic solvent/10% water. In a preferred aspect, the organic solvent is a water-miscible organic solvent, preferably ethanol.

The invention also provides a process to further purify CHDMAPP-Na$_2$,1H$_2$O, said method comprising the steps of:
 a. crystallizing CHDMAPP-Na$_2$,1H$_2$O, preferably according to the above described process; and
 b. recrystallizing the CHDMAPP-Na$_2$,1H$_2$O to obtain a substantially or essentially pure CHDMAPP-Na$_2$,1H$_2$O or CHDMAPP-Na$_2$,1H$_2$O composition.

The invention also provides a CHDMAPP composition under a crystallized form comprising less than 1% of impurities. In an aspect, said impurity is essentially CethylPP (B). The invention provides a substantially pure CHDMAPP disodium monohydrate (CHDMAPP-Na$_2$,1H$_2$O) composition, as well as pharmaceutical compositions comprising it. The invention provides a CHDMAPP composition free of CethylPP, as well as pharmaceutical compositions comprising it.

DESCRIPTION OF THE FIGURES

FIG. 10: Atomic coordinates of the CHDMAPP-Na$_2$,1H$_2$O crystalline phase (×10$^4$) and equivalent isotropic displacement parameters (Å$^2$×10$^3$) of the crystal structure. U(eq) is defined as one third of the trace of the orthogonalized Uij tensor.

DETAILED DESCRIPTION

Definitions

Figure 1:
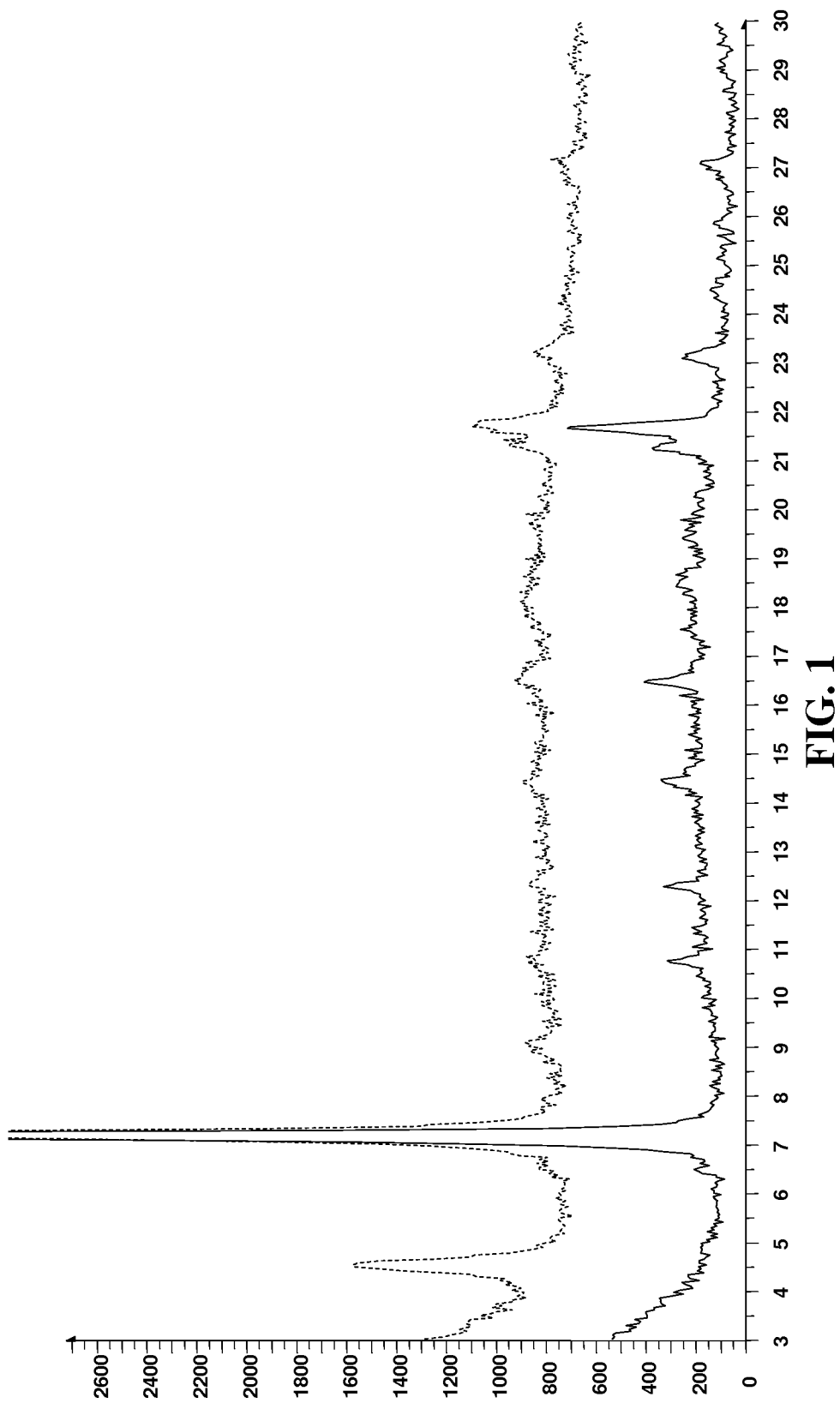
FIG. 1: XRPD pattern of the monohydrate of (2E)-1-hydroxy-2-methylpent-2-enyl-pyrophosphonate disodium (CHDMAPP-Na$_2$,1H$_2$O) (full line), and CHDMAPP monosodium salt (CHDMAPP-Na$_3$, dashed line). 2-Theta scale in axis, Lin (counts) in ordinates.

Where "comprising" is used, this can preferably be replaced by "consisting essentially of", more preferably by "consisting of".

As used in the specification, "a" or "an" may mean one or more. As used in the claim(s), when used in conjunction with the word "comprising", the words "a" or "an" may mean one or more than one. As used herein "another" may mean at least a second or more.

Where hereinbefore and hereinafter numerical terms are used, they are meant to include the numbers representing the upper and lower limits. For example, "between 1 and 3" stands for a range "from and including 1 up to and including 3", and "in the range from 1 to 3" would stand for "from and including 1 up to and including 3". The same is true where instead of numbers (e.g. 3) words denoting numbers are used (e.g. "three").

The term "about" or "approximately" usually means within 20%, more preferably within 10%, and most preferably still within 5% of a given value or range.

Within the context of the present invention, the term "% in total weight" means the mass of product incorporated in the formulation as compared to the total mass of the formulation.

Within the context of the present invention, a compound is considered stable as long as its initial purity has not decreased by more than 5%.

Within the context of the present invention, the shelf-life of the product is equal to the time necessary to reach the upper limit of the confidence interval for a relative purity of 95%.

Within the context of the present invention, "chemical purity" is defined as the chromatographic area purity obtained by High Performance Anion Exchange Chromatography analysis of said compound.

Within the context of the present invention, "phase purity" is defined as the amount of a given solid phase in a mixture of different phases.

Within the context of the present invention, "structural purity" is defined as the crystalline quality of a given phase (often given as a qualitative characteristic in comparison with a reference material). The reference Coquerel, Chemical Engineering and Processing 45 (2006) 857-862 discusses concepts of structural purity.

The composition of the invention is "substantially pure" when at least 98% of a sample is the particular phosphoantigen. Preferably, the phosphoantigen is "substantially pure" when at least 99% of a sample is the particular phosphoantigen.

The composition of the invention is "essentially pure" when at least 99.5% of a sample is the particular phosphoantigen. Preferably, the phosphoantigen is "essentially pure" when at least 99.9% of a sample is the particular phosphoantigen.

The composition of the invention is "substantially free" of another compound when the other compound(s) are present in an amount that is no more than 1% of the amount of the phosphoantigen composition.

The composition of the invention is "essentially free" of another compound when the other compound(s) are present in an amount that is no more than 0.5% of the amount of the phosphoantigen composition.

The composition of the invention is "free" of another compound when the other compound(s) are present in an amount that is no more than 0.1% of the amount of the phosphoantigen preparation. Alternatively, a phosphoantigen is "free" of another compound when the compound cannot be detected by HPAEC under conditions of maximum sensitivity in which a limit of detection is approximately 0.05% or less of the amount of the phosphoantigen preparation. Exemplary HPAEC methods are described herein in the section titled "Examples".

"Purified" CHDMAPP composition refers to substantially pure phosphoantigen, essentially pure phosphoantigen, or a salt thereof, or to phosphoantigen, or a salt thereof which is substantially free, essentially free, or free of another compound.

"Partially purified" CHDMAPP composition refers to phosphoantigen, or a salt thereof that is less than 90% pure.

The purity of CHDMAPP or another compound refers to the CHDMAPP or other compound prior to its formulation in a pharmaceutical composition. The purity may be measured by any means including nuclear magnetic resonance (NMR), liquid chromatography/mass spectroscopy (LC/MS) or microbiological assays. A preferred means for measuring the purity of CHDMAPP is by analytical high pressure liquid chromatography such as HPLC or HPAEC which measures the anionic purity.

Relative purity can be defined as the purity ratio between samples at $t_x$ and $t_0$ ($t_0$ being the initial date of quality control for batch delivery and $t_x$ the actual date of analysis).

The term crystalline (or crystallized) characterizes a solid phase in which a given compound (i.e. one or several molecules, or salt(s), or complex(es)) is periodically stacked with always the same spatial orientation, creating repeated intermolecular interactions with adjacent molecules.

The term polymorphism characterizes the ability for one given molecule (or salt, or solvate) to crystallize with different crystalline structures. It is worth noting that two polymorphic forms have exactly the same developed chemical formula. By extend, polymorphism may include the extreme case in which the molecule is in the amorphous state (i.e. not crystallized).

The term solvates (including hydrates) sometimes also referred to as pseudo-polymorphs, constitute another class of solids phases which differ from the genuine polymorphism by the presence of solvent molecules in stoichiometric or non stoichiometric amount inside the crystal lattice of the solid.

CHDMAPP Salts

Exemplary CHDMAPP compounds include monohydrates and anhydrous forms, as further described herein. The chemical name of CHDMAPP is (2E)-1-hydroxy-2-methylpent-2-enyl-pyrophosphonate and the chemical name CHDMAPP-Na$_2$ is (2E)-1-hydroxy-2-methylpent-2-enyl-pyrophosphonate disodium (hydrated or not). CHDMAPP-Na$_2$,0H$_2$O can be expressed as anhydrous (2E)-1-hydroxy-2-methylpent-2-enyl-pyrophosphonate disodium, while CHDMAPP-Na$_2$,1H$_2$O can be expressed as (2E)-1-hydroxy-2-methylpent-2-enyl-pyrophosphonate disodium monohydrate.

CHDMAPP Sodium Salt

An object of the present invention is a novel crystalline monohydrate of (2E)-1-hydroxy-2-methylpent-2-enyl-pyrophosphonate disodium (CHDMAPP-Na$_2$,1H$_2$O) compound of Formula (A):

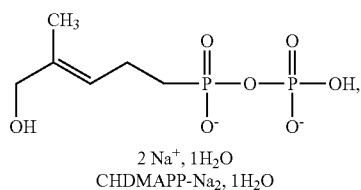

(Formula A)

2 Na⁺, 1H₂O
CHDMAPP-Na₂, 1H₂O (2E)-1-hydroxy-2-methylpent-2-enyl-pyrophosphonate (CHDMAPP) and methods for preparing the compound are described in U.S. Pat. No. 7,399,756, the disclosure of which is herein incorporated by reference. The counter-ion used with CHDMAPP is a sodium ion; sodium counter-ions are hydrophilic and present an enhanced solubility compared to organic salts described for example in patent application WO 07/039,635. Additionally, sodium counter-ions are physiologically innocuous and safe for administration to a subject; sodium counter-ion thus represents in that case the best compromise between biocompatibility, bioavailability, purity and stability.

CHDMAPP Disodium Salt

The CHDMAPP molecule presents three acidic functions, of which two functions have a strong pKa (pKa=2.1), and one function has a weak pKa (pKa=7.1). Each of these acidic functions can be coupled with a cation. Therefore, three stoichiometries of sodium salts of CHDMAPP may be prepared: A monosodium salt, a disodium salt and a trisodium salt.

Figure 2:
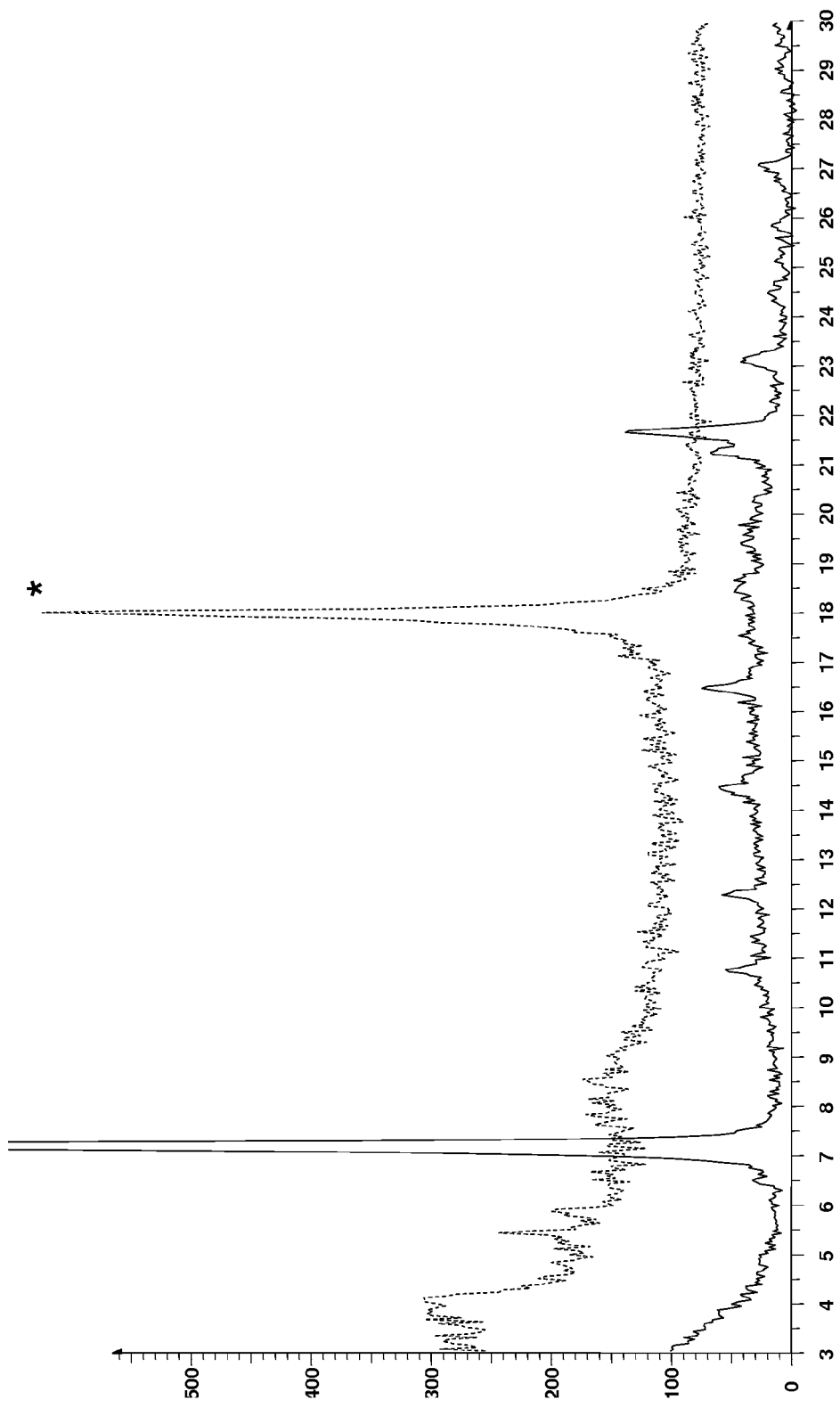
FIG. 2 XRPD pattern of the monohydrate of (2E)-1-hydroxy-2-methylpent-2-enyl-pyrophosphonate disodium (CHDMAPP-Na$_2$,1H$_2$O) (black full line), and CHDMAPP trisodium salt (CHDMAPP-Na$_3$, dashed line). The peak identified by the (*) is the Teflon™ diffraction peak of the sample holder. 2-Theta scale in axis, Lin (counts) in ordinates.

It was observed however, that the monosodium form has a low quality XRPD diagram, indicating a low crystallinity compound, as evidenced by comparison with the XPRD diagram of the CHDMAPP-Na₂-monohydrate, as shown in FIG. 1. The trisodium, on the other hand, leads to a very hygroscopic solid. The XRPD diagram of the trisodium, shown in FIG. 2, indicates a long range order resembling that observed with mesophases (i.e. liquid crystals). It was observed that among these forms, CHDMAPP disodium provides an outstanding highly crystalline composition.

CHDMAPP Disodium Monohydrate Salt CHDMAPP disodium can be provided as highly crystalline compositions. Several different forms of CHDMAPP disodium can be produced, either as an anhydrous salt or as a monohydrate salt, each of which will have distinct physical properties.

CHDMAPP-Na₂,0H₂O

Figure 3:
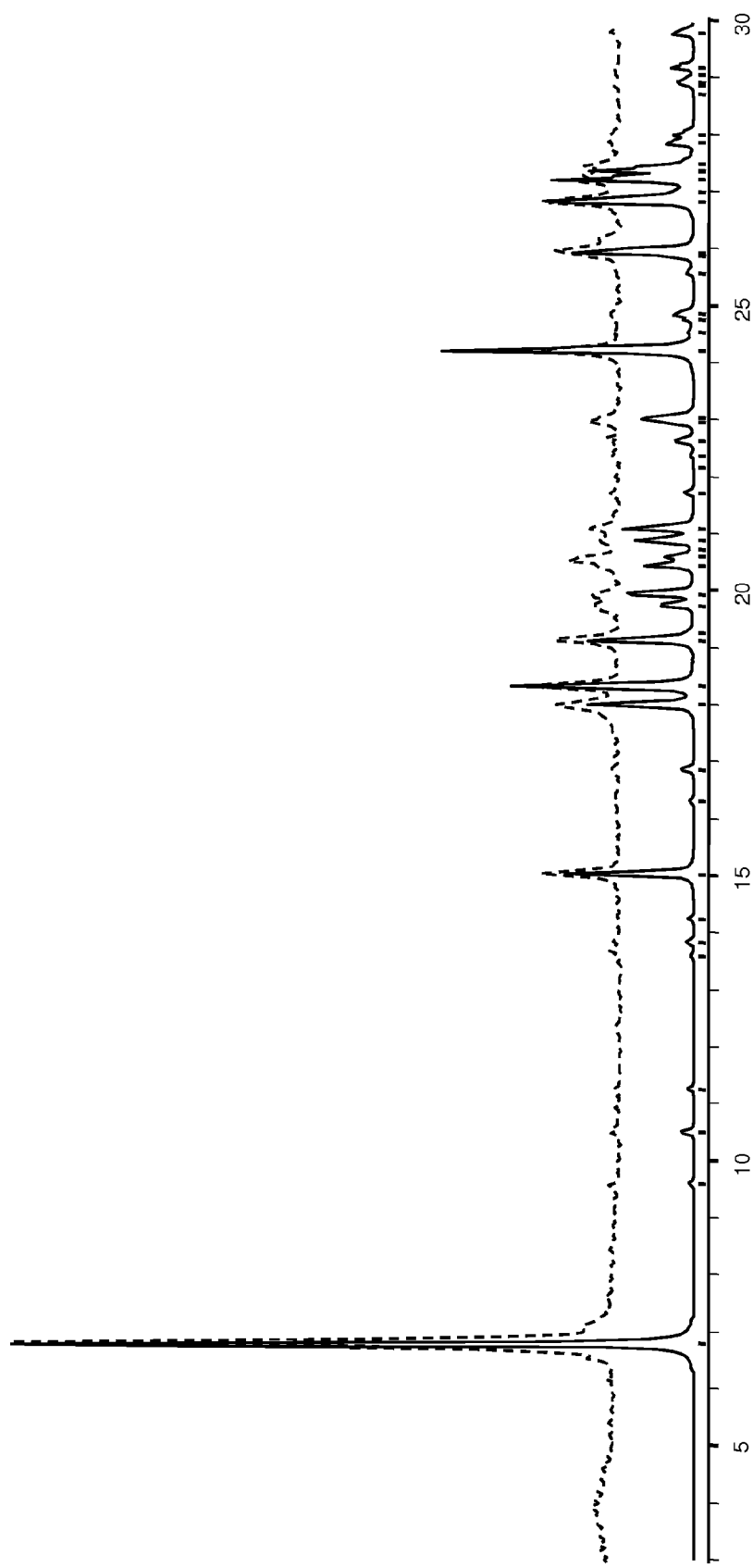
FIG. 3: Superimposition of X ray powder pattern for calculated (black full line) and experimental (black dashed line) CHDMAPP-Na$_2$,0H$_2$O anhydrous phase. 2-Theta scale is represented in axis.

The crystallization of the disodium salt in an organic solvent deprived of water (i.e. less than 1% in weight), will lead to the anhydrous phase CHDMAPP-Na₂,0H₂O. The specific XRPD pattern of this anhydrous phase is presented in FIG. 3. Specific d values either experimental (bolded) and theoretical (italic) are presented in the Table 1 below, the corresponding crystallographic parameters are presented in Table 2 below.

TABLE 1

XRPD data CHDMAPP-Na₂, 0H₂O

| Angle 2-theta ° | | d value Angstrom | | Intensity % | | h | k | l |
|---|---|---|---|---|---|---|---|---|
| 6.83 | *6.78* | 12.924 | *13.02* | 100 | *100.00* | 0 | 2 | 0 |
| 10.49 | *10.49* | 8.428 | *8.42* | 1 | *2.01* | 0 | 1 | 1 |
| 15.04 | *15.03* | 5.885 | *5.89* | 2.4 | *19.71* | 1 | 2 | 1 |
| 16.88 | *16.85* | 5.248 | *5.26* | 0.7 | *2.22* | 1 | 3 | 1 |
| 17.99 | *17.99* | 4.927 | *4.93* | 2 | *18.10* | 2 | 0 | 0 |
| 18.33 | *18.32* | 4.834 | *4.84* | 2.8 | *31.54* | 2 | 1 | 0 |
| 19.12 | *19.12* | 4.639 | *4.64* | 2.4 | *18.92* | 1 | 4 | 1 |

TABLE 1-continued

XRPD data CHDMAPP-Na₂, 0H₂O

| Angle 2-theta ° | | d value Angstrom | | Intensity % | | h | k | l |
|---|---|---|---|---|---|---|---|---|
| 19.73 | *19.73* | 4.496 | *4.50* | 1.2 | *5.93* | 0 | 5 | 1 |
| 19.97 | *19.93* | 4.441 | *4.45* | 1.4 | *12.11* | 0 | 0 | 2 |
| 20.45 | *20.44* | 4.3384 | *4.34* | 5.4 | *8.53* | 0 | 6 | 0 |
| 20.86 | *20.87* | 4.2535 | *4.25* | 1.2 | *10.30* | 2 | 1 | 1 |
| 21.10 | *21.08* | 4.2056 | *4.21* | 1.1 | *12.43* | 0 | 2 | 2 |
| 22.67 | *22.62* | 3.9181 | *3.93* | 0.7 | *3.41* | 2 | 4 | 0 |
| 24.18 | *24.20* | 3.6770 | *3.67* | 2.9 | *42.83* | 1 | 3 | 2 |
| 25.95 | *25.93* | 3.4299 | *3.43* | 6.3 | *21.94* | 0 | 7 | 1 |
| 26.84 | *26.82* | 3.3180 | *3.32* | 2.4 | *30.00* | 2 | 5 | 1 |
| 27.18 | *27.20* | 3.2773 | *3.28* | 1.8 | *25.44* | 2 | 1 | 2 |
| 27.36 | *27.36* | 3.2565 | *3.26* | 3.0 | *13.42* | 2 | 6 | 0 |
| 28.90 | *28.90* | 3.0863 | *3.09* | 0.7 | *3.07* | 2 | 3 | 2 |
| 29.18 | *29.17* | 3.0571 | *3.06* | 0.7 | *2.48* | 2 | 6 | 1 |

TABLE 2

| | |
|---|---|
| Chemical formula | Na₂[HO—CH₂—C(CH₃)=CH—(CH₂)₂—PO₂—O—PO₃H] |
| Molar mass/ g · mol⁻¹ | 304.07 |
| Crystalline system | Orthorhombic |
| Space group | P n a 2₁ (n° 33) |
| Z (number of molecules per unit cell) | 4 |
| Z' (number of molecules per asymmetric unit) | 1 |
| a/Å | 9.852(5) |
| b/Å | 26.049(5) |
| c/Å | 8.901(5) |
| V/Å³ | 2284.3(2) |
| d_calc/g · cm⁻³ | 1.768 |
| Temperature/K | RT |
| F(000)/e⁻ | 1248 |
| Absorption coefficient μ (MoKα₁)/mm⁻¹ | 0.475 |
| R reliability factor | 0.029 |

The anhydrous phase presents a well defined XRPD diagram, underlining a crystalline character. However, FIG. 5 underlines the lack of stability of the anhydrous salt under a varying relative humidity. The constantly increasing mass indicates that it is somewhat hygroscopic.

CHDMAPP-Na₂,1H₂O

Figure 4:
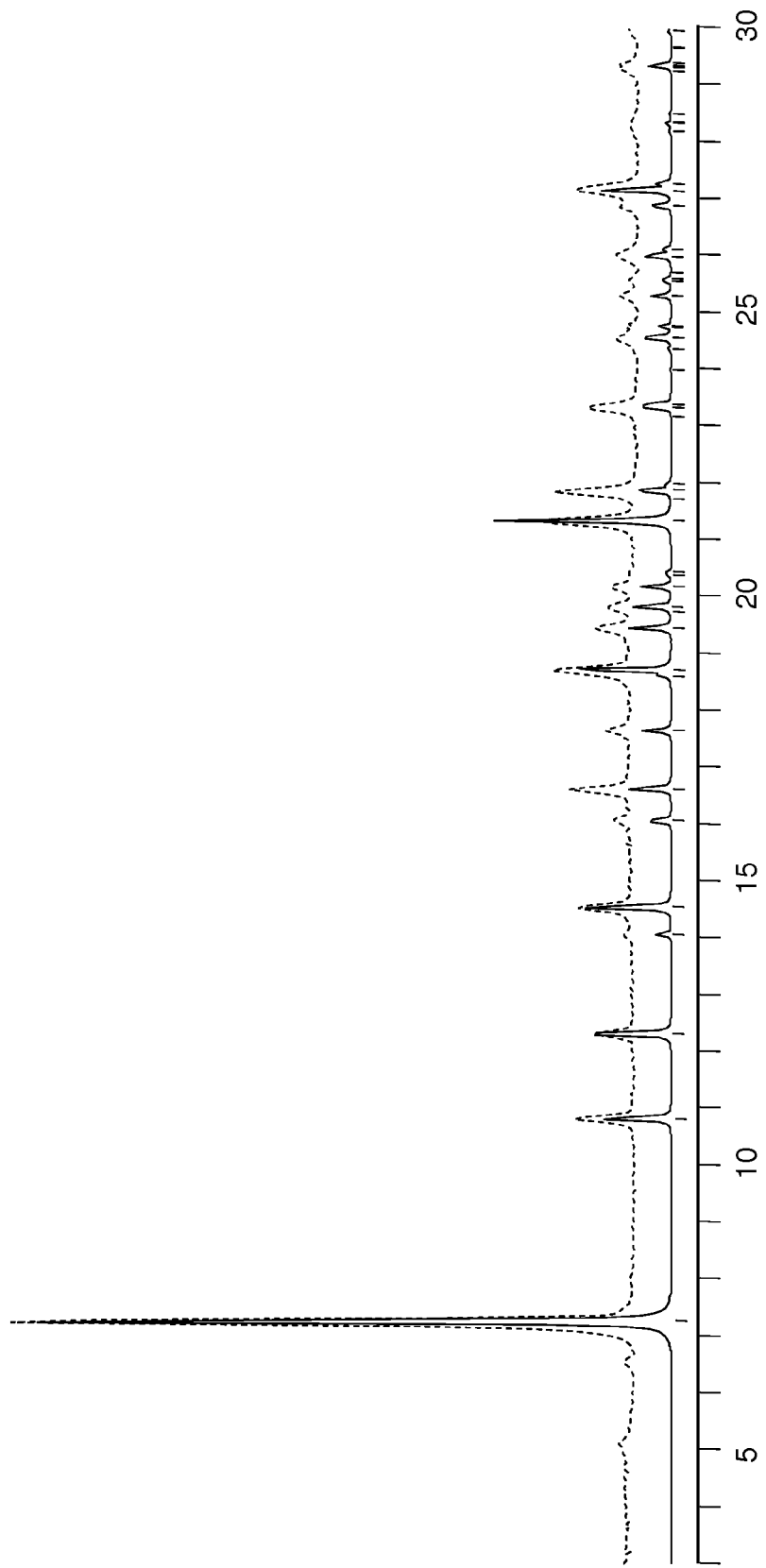
FIG. 4: Superimposition of X ray powder pattern for calculated (black full line) and experimental (black dashed line) CHDMAPP-Na$_2$ monohydrate phase. 2-Theta scale in axis.

The XRPD diagram of CHDMAPP-Na₂,1H₂O (cf. FIG. 4) shows very thin diffraction peaks, remarkably thinner (low full width at half maximum (fwhm)) than those of the anhydrous phase CHDMAPP-Na₂, which clearly demonstrates the better crystallinity of CHDMAPP-Na₂,1H₂O. This difference is even heightened for high two theta angle peaks, which demonstrates that CHDMAPP-Na₂,1H₂O has outstanding long range order properties (see table 3 below).

TABLE 3

| | 2 theta angle (°) | FWMH (°) |
|---|---|---|
| CHDMAPP-Na₂,1H₂O | 7.25 | 0.12 |
| | 21.32 | 0.104 |
| CHDMAPP-Na₂ | 6.78 | 0.17 |
| | 24.20 | 0.128 |

Table 4 below shows some characteristic XRPD peaks (experimental (bolded) and theoretical (italic) values are presented) of CHDMAPP-$Na_2$,$1H_2O$. This form has been obtained in a water/ethanol mixture.

TABLE 4

XRPD data CHDMAPP-$Na_2$, $1H_2O$

| Angle (2-Theta °) | d value (Angstrom) | | Intensity (%) | | h | k | l |
|---|---|---|---|---|---|---|---|
| 7.25 | 7.25 | 12.18 | 12.19 | 100 | 100 | 1 | 0 | 0 |
| 10.81 | 10.81 | 8.18 | 8.18 | 11.7 | 10.88 | 1 | 1 | 0 |
| 12.32 | 12.30 | 7.18 | 7.19 | 7.6 | 14.33 | 0 | 1 | 1 |
| 14.04 | 14.05 | 6.30 | 6.3 | 3.4 | 2.26 | −1 | 1 | 1 |
| 14.54 | 14.53 | 6.09 | 6.09 | 11.4 | 12.92 | 1 | 1 | 1 |
| 16.06 | 16.06 | 5.51 | 5.51 | 4.2 | 3.74 | 0 | 2 | 0 |
| 16.61 | 16.61 | 5.33 | 5.33 | 11.8 | 6.76 | 2 | 1 | 0 |
| 17.61 | 17.64 | 5.03 | 5.02 | 5.4 | 4.56 | 1 | 2 | 0 |
| 18.68 | 18.71 | 4.75 | 4.74 | 14.4 | 15.26 | −2 | 1 | 1 |
| 19.44 | 19.44 | 4.56 | 4.56 | 7.5 | 6.42 | 2 | 1 | 1 |
| 19.80 | 19.81 | 4.48 | 4.48 | 5.3 | 5.95 | −1 | 2 | 1 |
| 20.13 | 20.16 | 4.41 | 4.4 | 4.6 | 4.66 | 1 | 2 | 1 |
| 21.34 | 21.32 | 4.16 | 4.16 | 14 | 26.93 | −1 | 1 | 2 |
| 21.84 | 21.86 | 4.07 | 4.06 | 12.8 | 5.61 | 3 | 0 | 0 |
| 23.36 | 23.38 | 3.80 | 3.8 | 8.7 | 3.99 | −2 | 2 | 1 |
| 24.52 | 24.54 | 3.63 | 3.62 | 4.1 | 4.78 | −2 | 1 | 2 |
| 25.26 | 25.28 | 3.52 | 3.52 | 3.7 | 3.1 | 1 | 3 | 0 |
| 25.98 | 25.97 | 3.43 | 3.43 | 3.9 | 4.27 | 0 | 3 | 1 |
| 26.84 | 26.87 | 3.32 | 3.32 | 3.5 | 3.25 | −1 | 3 | 1 |
| 27.16 | 27.13 | 3.28 | 3.28 | 9.2 | 11.25 | 1 | 3 | 1 |

The monohydrate CHDMAPP disodium salt exhibits very interesting properties that are detailed below.

Figure 6:
FIG. 6: DVS diagram of the monohydrate of (2E)-1-hydroxy-2-methylpent-2-enyl-pyrophosphonate disodium (CHDMAPP-Na$_2$,1H$_2$O). The relative humidity is represent in percentage in axis, the change in mass is represent in percentage in ordinates. The compound according to the invention remains stable up to an 80% relative humidity value, where the mass of the sample raises rapidly and irreversibly. The very good stability above 80% RH underlines the great non-hygroscopicity of the compound according to the invention.

DVS analysis of CHDMAPP-$Na_2$,$1H_2O$ does not show any significant uptake of water up to 80% RH (shown in FIG. 6), which presumes a very good stability under humidity stress. To be considered as non-impacted by moisture, the guidelines of FDA or EMEA require that a drug compound should be stable up to 75% RH. FIG. 6 demonstrates that the compound is stable up to 80% RH, providing a stable compound with respect to water content in the sense of pharmaceutical guidelines.

Furthermore the monohydrate disodium salt provides a very efficient means to purify CHDMAPP. Synthesis of CHDMAPP yields ethylpyrophosphonate disodium (CethylPP-$Na_2$, compound of Formula B) as a main impurity, and purification by crystallization can be used to exclude impurities such as CethylPP-$Na_2$ from being incorporated in the crystals of CHDMAPP-$Na_2$,$1H_2O$. CHDMAPP compositions can therefore be obtained that are substantially free of, essentially free of, or free of, CethylPP-$Na_2$. Using the process according to the invention, the CHDMAPP-$Na_2$,$1H_2O$ can be obtained with less than 1%, preferably without any detectable amount (i.e. amount of impurity below the detection limit) of CethylPP-$Na_2$.

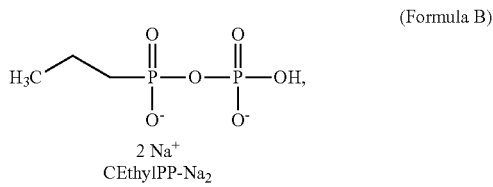

(Formula B)

CEthylPP-$Na_2$

Another advantage of the process of the invention is also that the crystallization step has a very good yield, e.g. a yield of more than 90%, more than 95%.

Figure 8:
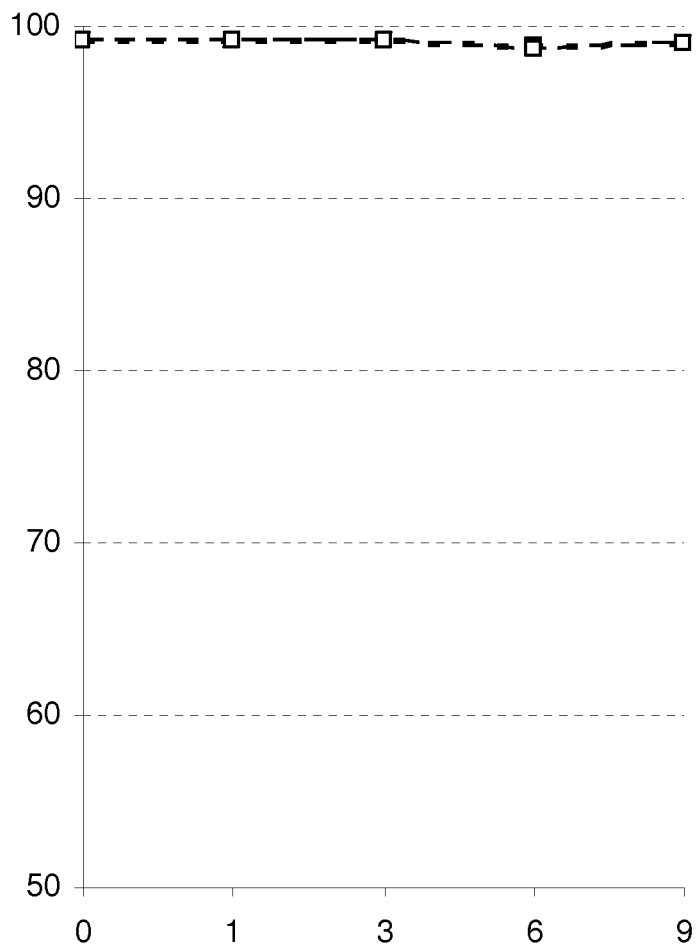
FIG. 8: The stability diagram of the monohydrate of (2E)-1-hydroxy-2-methylpent-2-enyl-pyrophosphonate disodium (CHDMAPP-Na$_2$,1H$_2$O) under various conditions. Full square line represent storage at 5° C., the empty squares lines represents storage at 25° C. and 60% relative humidity. Purity is represented in percentage in ordinates, time is represented in months in axis. The curves are almost linear and one can extrapolate a 28 months stability period for CHDMAPP purity of more than 95%.
Figure 9:
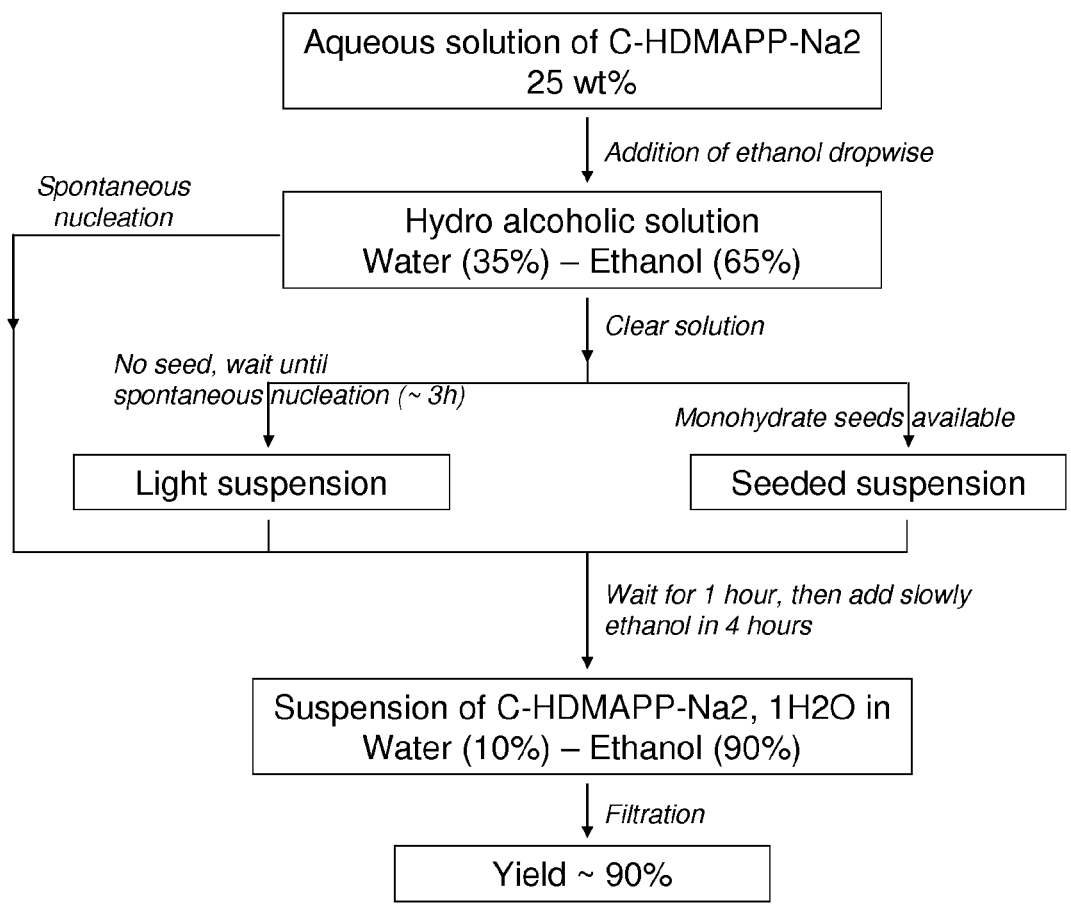
FIG. 9: Scheme of the crystallization process of the monohydrate of (2E)-1-hydroxy-2-methylpent-2-enyl-pyrophosphonate disodium (CHDMAPP-Na$_2$,1H$_2$O).

This novel crystalline form is also thermodynamically very stable; one does not observe any spontaneous phase transformation after more than 6 months, even in harsh conditions (25° C., 60% RH) and the above mentioned intrinsic phase properties are preserved over a wide range of experimental conditions (i.e. high R.H., high and low temperatures). As shown in example 3 and FIG. 8, CHDMAPP-$Na_2$,$1H_2O$ guarantees the chemical stability of CHDMAPP over long storage duration. By extrapolation, the chemical stability of CHDMAPP-$Na_2$,$1H_2O$ can be estimated at ca. 28 months at 5% (chemical purity higher than 95%).

By means of comparison, CHDMAPP compound in solution in water at 5% in weight (1.25 g of CHDMAPP in 25 g of water) has a half-life of 2.6 days at 55° C. The crystalline phase thus provides a dramatic improvement of the stability and of the storage capabilities of the drug product.

Figure 7:
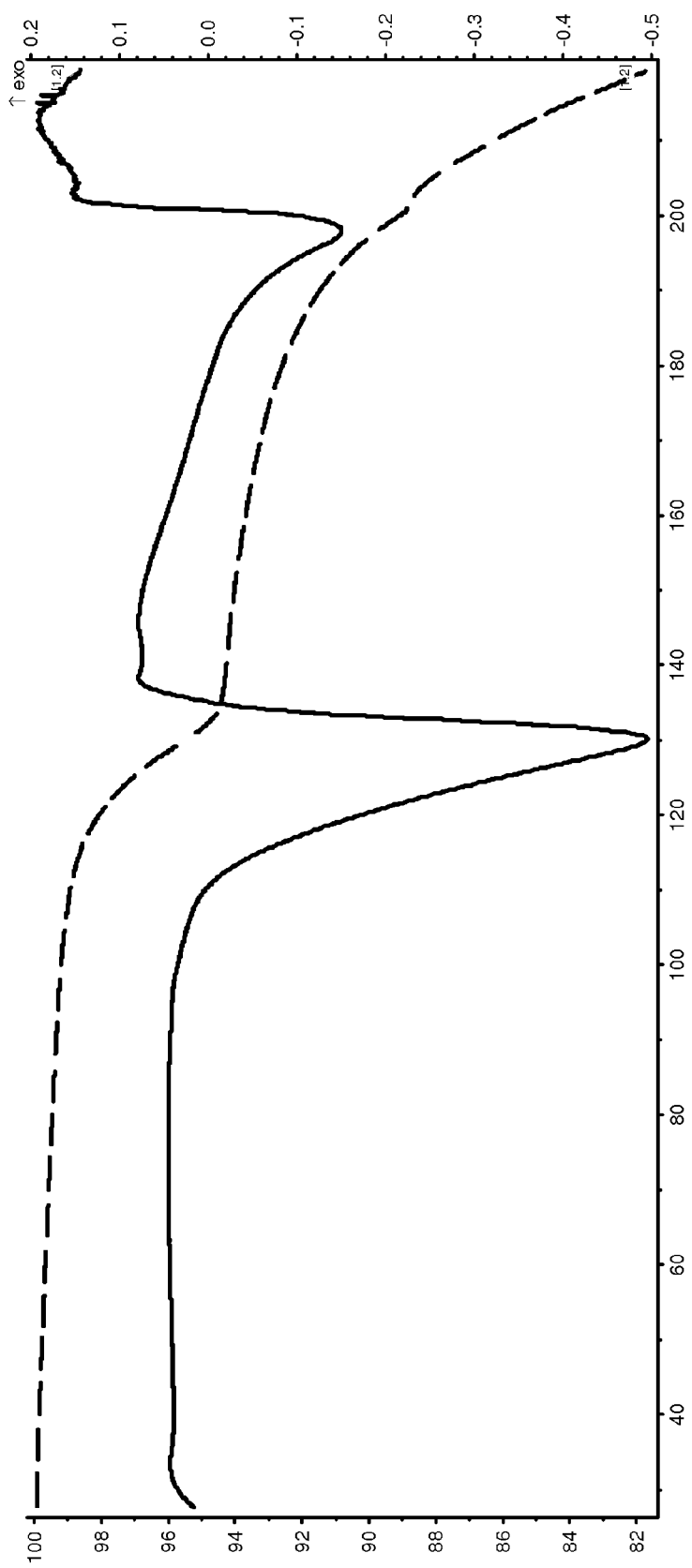
FIG. 7: TGA-DSC diagram of the monohydrate of (2E)-1-hydroxy-2-methylpent-2-enyl-pyrophosphonate disodium (CHDMAPP-Na$_2$,1H$_2$O) the compound is stable until the onset temperature of 115.7° C. Parameters for the complex peak obtained by TGA-DSC analysis: Area: −223.2 J/g, Peak: 130.2° C., Onset: 115.7° C., End: 134.3° C., Width: 13.7° C. (37.000%), Height: 0.6084 mW/mg. Dashed line TGA signal (left ordinate in percentage); full line DSC signal (right ordinate in mW/mg), temperature in celcius in represented in axis.

The monohydrate disodium salt is also very stable upon raise in temperature and can be heated up to 115° C. without undergoing dehydration or fast degradation, as shown in FIG. 7 (TGA/DSC profile).

The compound according to the invention also presents very desirable handling properties, as the inventors obtain a fine, non aggregated and homogeneous white powder. Furthermore, no interactions with commonly used excipients have been underlined; the compound can be processed according to standard formulation techniques.

The crystalline monohydrate of (2E)-1-hydroxy-2-methyl-pent-2-enyl-pyrophosphonate disodium (CHDMAPP-$Na_2$, $1H_2O$) compound was characterized by various physical and chemical analyses, as follows. While it will be appreciated that the physical form of the CHDMAPP compositions can be defined by any one or combination of physical characteristics, the XRPD pattern and melting point data, independently or in combination, provide convenient and accurate means for characterizing the solid phase. However any other physical characteristics, either alone or in combination, or furthermore in combination with XRPD and/or melting point analysis, can be used to describe the compounds, including for example water content, DVS and crystallographic parameters.

Content in Water

Karl Fischer analysis of CHDMAPP-$Na_2$,$1H_2O$ indicates a water content at approximately 6% in weight, which corresponds to the stoichiometry of a monohydrate of the CHDMAPP-$Na_2$ compound (one water molecule per CHDMAPP molecule in the crystal lattice).

Differential Scanning Calorimetry—Thermogravimetry

The stability range was assessed using Differential Scanning calorimetry (DSC), using a Netzsch STA 449C apparatus, as is described in detail hereinafter, and having a standard deviation of ±0.5° C. The person skilled in the art will appreciate that alternative readings of the melting point may result from the use of other types of DSC equipment and/or the use of other system under conditions different to those described below.

The compound is stable up to the onset of the endothermic peak at 115.7° C. Under the onset temperature of about 115.7° C., equilibrium takes place and a slow and reversible partial dehydration of the crystal occurs, without modifying the crystal structure of the compound. The peak is at its maximum at a temperature of about 13.2° C. When the temperature is above 115.7° C., the dehydration is completed (loss of mass 5.62%, corresponding to one molecule of water detected by thermogravimetry (TGA)), destabilizing the crystalline structure and initializing the chemical degradation of the compound (second loss in mass in the TGA analysis, occurring continuously and rapidly). In a preferred aspect, the physical form of the present invention is defined by means of the XRPD and by means of its thermal behaviour.

The crystalline monohydrate of (2E)-1-hydroxy-2-methyl-pent-2-enyl-pyrophosphonate disodium (CHDMAPP-$Na_2$, 1H$_2$O) can be characterized as having a physical form stable up to a temperature of 115.7° C., where an endothermic peak, characterized as a dehydration peak, is detected.

DVS

Figure 5:
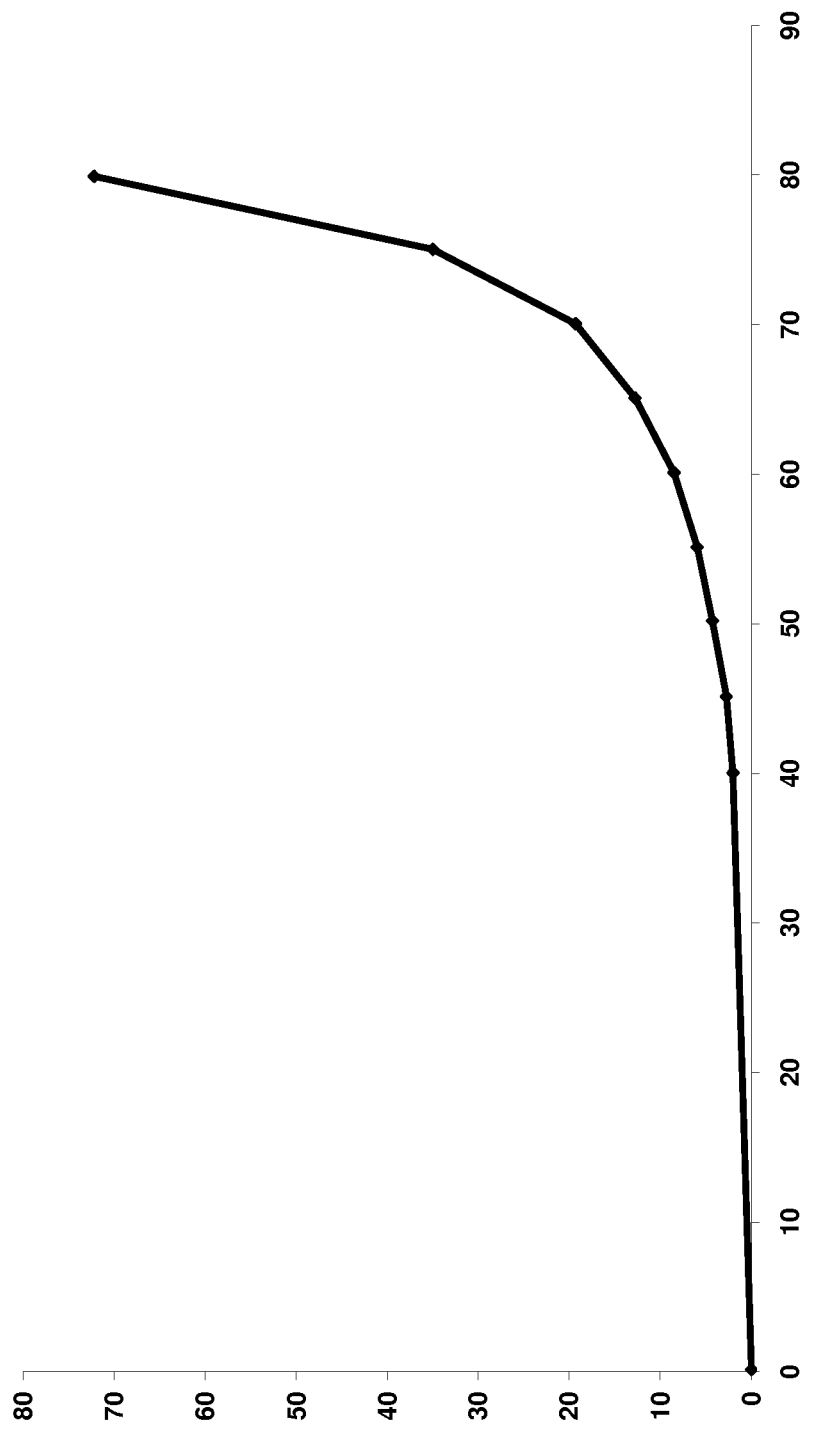
FIG. 5: DVS diagram of the anhydrous phase of (2E)-1-hydroxy-2-methylpent-2-enyl-pyrophosphonate disodium (CHDMAPP-Na$_2$,0H$_2$O). The relative humidity is represent in percentage in axis, the change in mass is represent in percentage in ordinates. The constant raise in mass underlines a hygroscopic property that is highly undesirable for a drug product.

DVS analysis at 20° C. indicated, as shown in FIG. 5, that the compound is stable up to about 80% RH, then the compounds begins to be deliquescent. The crystalline form therefore shows good stability with respect to water and can be described as non-impacted by water according to the guidelines of FDA (Food and Drug Administration) or EMEA (European Medicine Agency) which require that a drug compound should be stable up to 75% RH.

XRPD Pattern

The XPRD pattern of the crystalline monohydrate of (2E)-1-hydroxy-2-methylpent-2-enyl-pyrophosphonate disodium (CHDMAPP-Na$_2$,1H$_2$O) which physical form has X-ray diffraction peaks at 28 (2-theta)=7.25; 10.81; 12.32; 14.04; 14.54; 16.06; 16.61; 17.61; 18.68; 19.44; 19.80; 20.13; 21.34; 21.84; 23.36; 24.52; 25.26; 25.98; 26.84; 27.16.

The XRPD pattern was obtained using a Siemens D5005 equipment as described in details herein. The person skilled in the art will appreciate that different equipment and/or different conditions may result in different data as mentioned hereinafter. It will also be appreciated that some peaks may not be detectable when the product is in a pharmaceutical formulation. It will be appreciated that a CHDMAPP crystalline phase according to the invention is identified when at least 1, 2, 3, 4, 5, 6, 7, 8, 9, 10, 11, 12, 13, 14, 15, 16, 17, 18, 19 or all of the peaks (2-theta angles) of the XRPD pattern are detected in a XRPD diagram.

Crystallographic Parameters of CHDMAPP-Na$_2$,1H$_2$O

Crystallographic parameters obtained according to the described procedure allow resolving the crystal structure of CHDMAPP-Na$_2$,1H$_2$O. The reliability factor R is 0.00358, which underlines a very good description of the crystal structure of the solid phase.

TABLE 5

| | |
|---|---|
| Chemical formula | Na$_2$[HO—CH$_2$—C(CH$_3$)=CH—(CH$_2$)$_2$—PO$_2$—O—PO$_3$H],H$_2$O |
| Molar mass/g·mol$^{-1}$ | 322.09 |
| Crystalline system | Monoclinic |
| Space group | P 2$_1$/c (n° 14) |
| Z | 4 |
| Z' (asymmetric unit) | 1 |
| a/Å | 12.201(1) |
| b/Å | 11.03(1) |
| c/Å | 9.495(1) |
| β (°) | 92.928(2) |
| V/Å$^3$ | 1276.1(3) |
| d$_{calc}$/g·cm$^{-3}$ | 1.677 |
| Temperature/K | RT |
| F(000)/e$^-$ | 664 |
| Absorption coefficient μ (MoKα$_1$)/mm$^{-1}$ | 0.436 |
| R reliability factor | 0.0358 |
| Crystal habit | needle |
| Crystal colour | colourless |
| Approximate crystal size/mm | 0.5 × 0.1 × 0.06 |

Figures 11, 12:
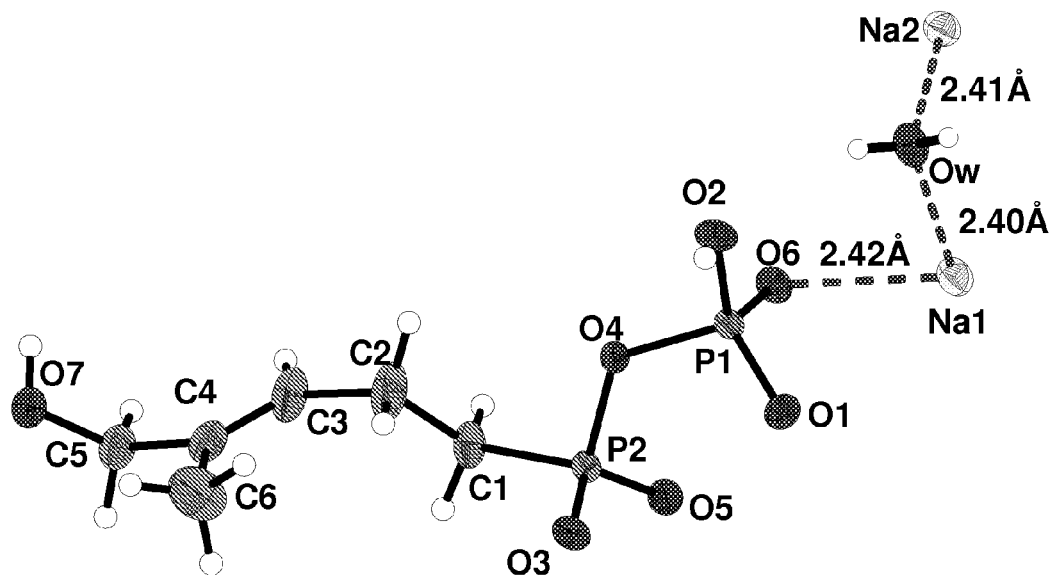
FIG. 11: Anisotropic displacement parameters (Å$^2$×10$^3$). The anisotropic displacement factor exponent takes the form: $-2\pi^2 [h^2 a^{*2} U11+ \ldots +2 h k a^* b^* U12]$.
FIG. 12: Three dimensional representation of the monohydrate of (2E)-1-hydroxy-2-methylpent-2-enyl-pyrophosphonate disodium (CHDMAPP-Na$_2$,1H$_2$O). Asymmetric unit of Na$_2$-[HO—CH$_2$—C(CH$_3$)=CH—(CH$_2$)$_2$—PO$_2$—O—PO$_3$H, 1H$_2$O with atoms labels and ellipsoidal contribution (50% of probability).
Figure 13:
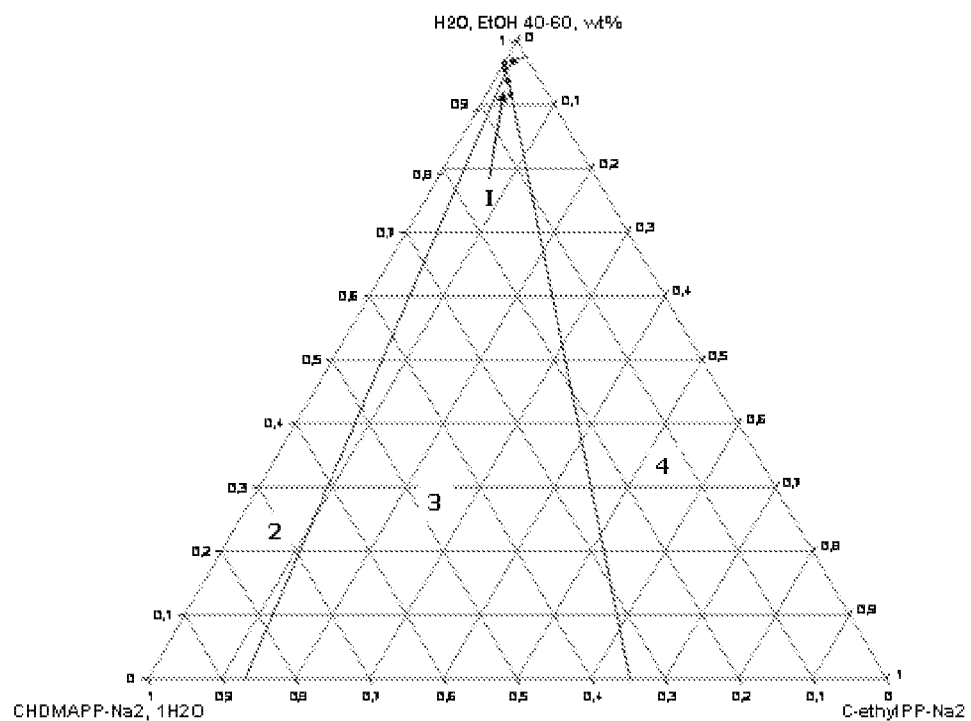
FIG. 13A: Ternary phases diagram [CHDMAPP-Na$_2$, 1H$_2$O/C-ethylPP-Na$_2$/(water-ethanol 40-60, wt %)] determined at 20° C. using first DITA measurements diagram. Full lines represent the hypothectical limits of phases stability domains, domain 1 corresponds to the undersaturated solution, domain 2 corresponds to the solid solution issued from CHMDAPP-Na$_2$, 1 H$_2$O and the saturated solution, domain 3 corresponds to a mixture of the solid solution issued from CHDMAPP-Na$_2$,1H$_2$O, and the saturated solution and of the solid solution issued from C-ethylPP-Na$_2$, domain 4 corresponds to the solid solution issued form C-ethylPP-Na$_2$ and the saturated solution.
FIG. 13B: Focus on the ternary phases diagram [CHDMAPP-Na$_2$,1H$_2$O/C-ethylPP-Na$_2$/(water-ethanol 40-60, wt %)], in this representation, domain 1 (undersaturated solution) is more clearly visible.
Figure 13B:
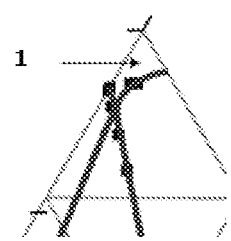
Figure 14:
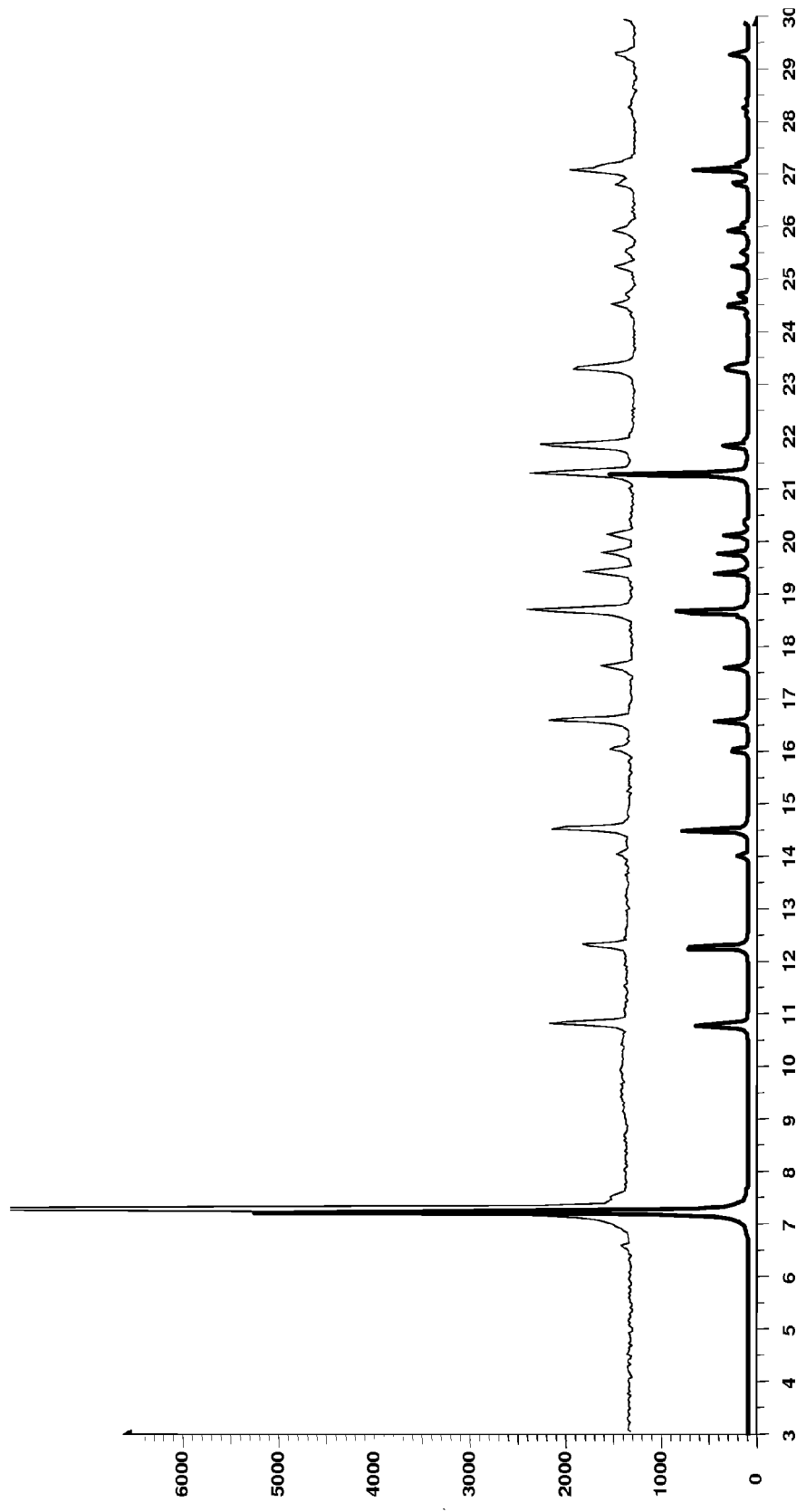
FIG. 14: X ray powder diffraction analysis of calculated CHDMAPP-Na$_2$-1H$_2$O (bold line) and CHDMAPP-Na$_2$-1H$_2$O stored 3 months at 40° C., 75% RH (thin line). 2-Theta scale in axis, Lin (counts) in ordinates. The crystalline structure of the compound has not been modified over a 3 months storage in challenging conditions.
Figure 15:
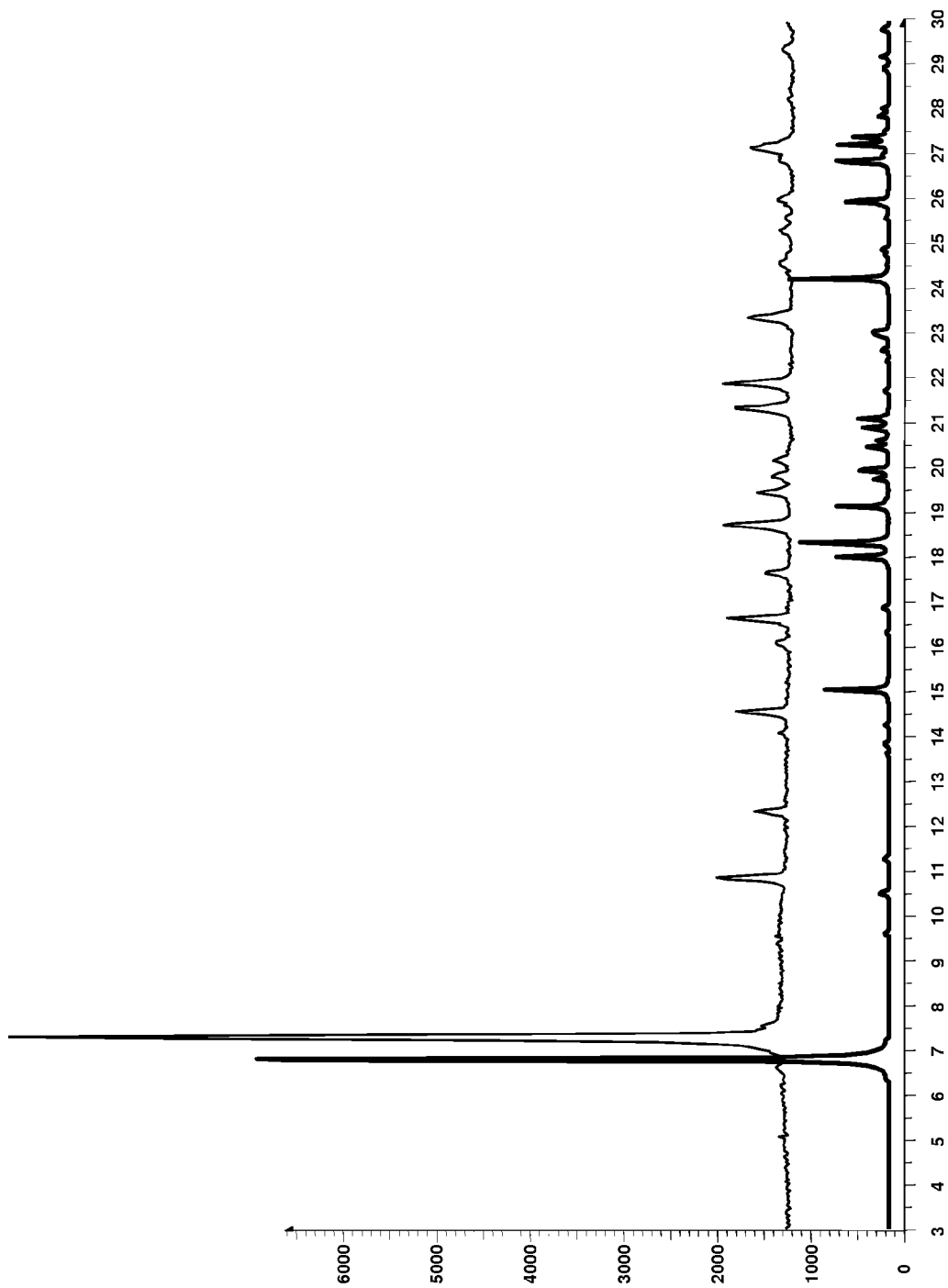
FIG. 15: X ray powder diffraction (XRPD) analysis of calculated CHDMAPP-Na$_2$0H$_2$O (bold line) and CHDMAPP-Na$_2$,0H$_2$O stored 3 months at 40° C., 75% RH (thin line). 2-Theta scale in axis, Lin (counts) in ordinates. After a three months storage, the crystalline structure of the compound has been completely modified, underlining the lack of stability of the CHDMAPP-Na$_2$,0H$_2$O amorphous form.

FIG. 10 lists the atomic coordinates (×10") and equivalent isotropic displacement parameters (Å$^2$×10$^3$) of the crystal structure. FIG. 11 lists the anisotropic displacement parameters (Å$^2$×10$^3$). These data underline the fact that the crystal structure of the invention is perfectly defined and characterized. FIG. 12 is the three dimensional representation of the molecule in its crystalline structure.

Process of Crystallization

The CHDMAPP compounds according to the invention can be made using the methods described in the Examples section herein. Briefly, methods for making CHDMAPP compounds of the invention may generally comprise:

(1) diluting CHDMAPP-Na$_2$ in water,
(2) adding an organic solvent until the formation of crystals, and
(3) isolating the crystals,
(4) drying the crystallized CHDMAPP compound.

In particular, the invention provides methods of making CHDMAPP-Na$_2$,1H$_2$O compound comprising:

(1) diluting CHDMAPP-Na$_2$ in water,
(2) adding an organic solvent until the formation of crystals, and
(3) isolating the crystals,
(4) drying the crystallized CHDMAPP-Na$_2$,1H$_2$O.

The invention also provides a method of further purifying CHDMAPP-Na$_2$,1H$_2$O, said method comprising the steps of:

(a) crystallizing CHDMAPP-Na$_2$,1H$_2$O, preferably according to preceding steps (1) to (4); and
(b) recrystallizing the CHDMAPP-Na$_2$,1H$_2$O to obtain a substantially or essentially pure CHDMAPP-Na$_2$,1H$_2$O or CHDMAPP-Na$_2$,1H$_2$O composition, and/or advantageously a CHDMAPP-Na$_2$,1H$_2$O or CHDMAPP-Na$_2$,1H$_2$O composition substantially or essentially free of impurities.

Optionally, the process comprises a step (3'), where the filtration cake is washed.

Optionally any of the methods can further comprise a step of formulating a drug product, preferably by adding a pharmaceutically acceptable excipient, for example formulating the CHDMAPP-Na$_2$-1H$_2$O composition as a drug product in a unit dosage form such as tablets, pills, capsules, powders, granules, sterile solutions or suspensions, metered aerosol or liquid sprays, drops, ampoules, auto-injector devices or suppositories.

The method used herein to prepare the compounds generally involved the steps of:

(1) diluting CHDMAPP-Na$_2$ in water, or providing CHDMAPP-Na$_2$ in solution,
(2) adding slowly and drop wise an organic solvent, such as but not limited to a water-miscible organic solvent, i.e. an alcohol such as for example ethanol, up to the point where nucleation can take place,
(3) adding more organic solvent slowly to allow the rest of CHDMAPP to crystallize
(4) washing the crystals by a water-alcohol mixture for instance: 4%-96% water ethanol azeotropic mixture,
(5) drying the solid for instance at room temperature under a ventilated normal atmosphere
(6) isolating the CHDMAPP-Na$_2$,1H$_2$O crystals obtained.

In a preferred embodiment, in step (1), CHDMAPP is initially diluted in water at 25% wt. The CHDMAPP-Na$_2$ in solution can be obtained in an embodiment by stemming from an ion exchange resin.

The addition of the organic solvent in step (2) can optionally be stopped when the hydroorganic solution has a composition close to 35% water/65% organic solvent. In the particular protocols used herein, the addition step (2) lasts for about at least one hour. The medium is gently stirred and then allowed to rest until the formation of crystals. In particular, the kinetics of anti-solvent addition of step (2) is adjusted so that the solid which crystallizes does not exhibits XRPD peaks at 7.2°, 10.6° and 16.4° (2 theta scale copper anticathode). These undesirable peaks are observed when the addition of the anti-solvent is done is a precipitated manner An optional step (2') can be included, where the medium is seeded with CHDMAPP-$Na_2,1H_2O$ crystals to expedite the nucleation step.

In the particular protocols used herein, step (3) takes place for a length of time of at least about 4 hours. The organic solvent was added in step (3) until the composition of the solution reaches 90% organic solvent/10% water.

In another aspect, the invention provides methods of making CHDMAPP-$Na_2,0H_2O$ compound comprising:
(1) suspending CHDMAPP-$Na_2$ in on organic solvent,
(2) triturating the suspension and allowing it to rest for some time,
(3) isolating the crystals, and
(4) drying the crystallized CHDMAPP-$Na_2,0H_2O$.

In one embodiment, the suspension is allowed to rest for 6, 9, 12 or more hours before performing step (3).

For all methods of the invention, the isolation step can be performed by filtration or centrifugation. In one embodiment, the organic solvent is a water-miscible organic solvent, such as but not limited to acetone, methanol, ethanol. In a preferred embodiment, the solvent is ethanol. In an embodiment, step (4) is performed by filtration, and the crystals are dried cautiously.

Composition and Dosage Unit Forms, Uses of the Composition of the Invention

Once a CHDMAPP-$Na_2$ compound is obtained, it can be formulated as a drug product, i.e. an active pharmaceutical ingredient (API), typically by adding a pharmaceutically acceptable excipient. With all pharmaceutical compounds and compositions, the chemical and physical stability of a drug compound is important in the commercial development of that drug substance. The stability is crucial for example in determining the validity period of the pharmaceutical specialty; this period is that in which the drug can be administered without any risks either due to the presence of an excessive amount of potentially dangerous degradation products or risks due to an unacceptably low content of the active principle with respect to the stated amount. The high stability of a drug substance in the above pharmaceutical compositions at different conditions of storage represents therefore an additional advantage both to the patient and to the manufacturer since storage in controlled conditions is avoided as well as the frequent replacement of expired specialty. The CHDMAPP-$Na_2$ compounds, and especially CHDMAPP-$Na_2,1H_2O$, in view of their stability, are particularly well adapted to the preparation of solid dosage forms; such dosage forms often involve manufacturing processes which requires milling of the drug or other particle size reduction steps such as micronization to achieve drug material with uniform particle size and surface area. Unstable materials often undergo polymorphic changes, and other undesirable properties such as hygroscopicity, stickiness, chemical changes, etc. Likewise, purity is important, and compositions having few impurities (e.g. ethylpyrophosphonate (CethylPP)) will be advantageous for the preparation of both solid and other dosage forms (e.g. solutions). Furthermore, the compound obtained according to the invention also presents desirable properties for manipulation, including being in a solid form, having a good compressibility, no electrostatic burden, rendering the compound suited for many formulations i.e. tabletting, measure and dilution, etc. The compound according to the invention is also well defined and characterized enabling improved control of the amount of active pharmaceutical ingredient administered to a patient. CHDMAPP-$Na_2,1H_2O$ can therefore be easily formulated as a drug product in unit dosage forms such as tablets, pills, capsules, powders, granules, or suspensions. The compositions can be used for oral, parenteral, intranasal, sublingual, or rectal administration or for administration by inhalation or insufflation. Formulation of the compositions according to the invention can be carried out according to methods known from the art, for example, as described in Remington's Pharmaceutical Sciences, $18^{th}$ ed., Mack Publishing, Easton, Pa. (1990). The compound according to the invention can be formulated using one, more or all of the following pharmaceutically acceptable materials: an excipient, a diluent, a disintegrant, a plasticizer, a colorant, a dosing vehicle, or any combination thereof.

CHDMAPP compositions of the invention are advantageous for preparing pharmaceutical forms suitable for oral administration because these are often presented as tablets (including without limitation scored or coated tablets), pills, granules, lozenges, caplets, capsules, chewable tablets, powder packets, cachets, troches, wafers, etc. Tablets and capsules represent the most advantageous solid oral dosage unit forms, in which case solid pharmaceutical excipients are used. If desired, tablets can be coated by standard aqueous or non-aqueous techniques. These dosage forms can be prepared by any of the methods of pharmacy. In general, pharmaceutical compositions and dosage forms are prepared by uniformly and intimately admixing the active ingredient(s) with liquid carriers, finely divided solid carriers, or both, and then shaping the product into the desired presentation if necessary. For example, a tablet can be prepared by compression or molding. Compressed tablets can be prepared by compressing in a suitable machine the active ingredient(s) in a free-flowing form, such as a powder or granules, optionally mixed with one or more excipients. Molded tablets can be made by molding in a suitable machine a mixture of the powdered compound moistened with an inert liquid diluent.

Optionally, in another aspect, the present invention relates to a novel monohydrate crystalline phase of CHDMAPP-$Na_2$, intended for the treatment of a disease, especially a proliferative disease, and more preferably a solid tumor, particularly a solid tumor having metastases. The composition according to the invention is also suited for the treatment of infectious diseases. Preferably, the monohydrate crystalline phase of CHDMAPP-$Na_2$, is administered in an amount and under conditions sufficient to stimulate the expansion of the γδ T cell population in a subject, particularly to reach 30-90% of total circulating lymphocytes, typically 40-90%, more preferably from 50-90%. Percentage of total circulating lymphocytes can be determined according to methods known in the art.

In another embodiment, the present invention relates to a monohydrate crystalline phase of CHDMAPP-$Na_2$ administered in an amount and under conditions sufficient to stimulate the expansion of the γδ T cell population in a subject, particularly to increase by more than 2-fold the number of γδ T cells in a subject, typically at least 4, 5 or 10-fold, more preferably at least 20-fold, conjointly or not with a IL-2 at a dose of about 1 to 9 MIU total daily in human.

In another aspect, the present invention relates to methods for the treatment of a disease, especially a proliferative disease, and more preferably a solid tumor, particularly a solid tumor having metastases, where a monohydrate crystalline phase of CHDMAPP-$Na_2$ is administered in an amount and under conditions sufficient to stimulate the expansion of the γδ T cell population in a subject, particularly to reach a circulating γδ T cell count of at least 500 γδ T cells/$mm^3$ in a subject, typically at least 1000 γδ T cells/$mm^3$, more preferably at least 2000 γδ T cells/$mm^3$.

In another aspect, the compound of the invention can be administered together with at least a second therapeutic agent, as disclosed in PCT publication no. WO2004/050096, WO2005/102385, WO2007/057440, WO2008/059052 or WO2008/006895.

Examples of dosages, uses, and administration regimens of CHDMAPP compositions for use as γδ T cell activators are provided in U.S. Pat. No. 7,399,756, the disclosure of which is herein incorporated by reference, for the treatment of cancer in PCT publication no. WO2004/050096, the disclosure of which is incorporated herein by reference and for use as adjuvant in combination with an antigen for the treatment or prevention of disease, particularly infectious disease and cancer, in PCT publication no. WO 2005/102385, the disclosure of which is incorporated herein by reference.

EXAMPLES

Further aspects and advantages of this invention are disclosed in the following experimental section, which should be regarded as illustrative and not limiting the scope of this application.

Procedures

Procedure for XRPD Analyses

X-Ray Powder Diffraction measurements were carried out by using a SIEMENS D5005 diffractometer (Bruker analytical X-Ray Systems, D-76187 Karlsruhe, Germany) with a Bragg Brentano geometry, in theta-theta reflection mode. The instrument is equipped with a X-Ray tube (copper anticathode, 40 kV, 30 mA, $K_{\alpha 1}$ radiation: 1.5406 Å, $K_{\alpha 2}$ radiation: 1.5444 Å), a nickel filter and a scintillation detector. The diffraction patterns were collected by steps of 0.04° (2-theta) over the angular range 3°-30°, with a counting time of 4 s per step. No internal standard was used but a sample of quartz was analyzed as an external standard. The temperature of the sample was either the room temperature or accurately monitored when heating was required. DIFFRAC PLUS Edit Job software (v. 2.00) was used as control software and data processing was performed by using the Eva software (v. 9.0 and v. 10.0).

Procedure for TG/DSC Analyses

TG/DSC measurements were carried out by using a NETZSCH STA 449C Jupiter Thermogravimetric Analyzer (NETZSCH, D-95100 Selb, Germany) equipped with a low temperature furnace. The purge gas used was helium (gas flow=50 mL/min) and the reference material was an empty aluminum pan without cap. The samples were weighed in open aluminum pans, and then placed in the analyzer. The analyses were performed within various temperature ranges using a 2°.min$^{-1}$ heating rate. PROTEUS software was used for the acquisition and data processing (v. 4.7.0).

Procedure for Hygroscopicity and Moisture Measurements

Moisture sorption isotherms of the crystalline phases were obtained by using a DVS-1 automated water sorption analyzer (Surface Measurements Systems, Alperton, Middlesex, United Kingdom). The reference material was an empty glass pan and the total gas flow was 200 sccm.min$^{-1}$ (Standard Cubic Centimeters per minute). Temperature of analysis was 20° C. For each measurement, precisely ca. 15 mg of the sample were weighed in a glass pan beforehand allowed for the tare, then placed in the analyzer.

As a first stage, dry nitrogen (0% R.H) was applied until constant weight of the sample in order to eliminate adsorbed or absorbed water (potential dehydration). Then, mass variations were recorded while R.H. was increased by steps of 10% R.H. The automated analyzer was allowed to start the following step as soon as the mass variation of the sample was less than $5.10^{-4}$ mg.min$^{-1}$. The upper limit was adjusted below the deliquescence of the compound and never exceeded 90% R.H.

DVSWin (v 2.18) was used as control and data collection software whereas data processing was performed by using DVS Standard Analysis Suite (v 4.3).

Further parameters used in DVS procedures are as follows:
Protocole Dynamic Vapor Sorption/Appareil 'Surface Measurements Systems)=
Automated Water Sorption Analyzer'/model: DVS-1
Analysis method:
step mode,
Temperature: 20° C.
step dm/dt<0.0005 (mg/min)
First stage R.H.=0%
Last Stage R.H.=90%
Minimum Stage: 20 min
Maximum Stage: 120 min
Total Gas Flow: 200
Nitrogen: 200 Bars, H2O<3 ppm, O2<2 ppm, Réf. Nitrogen N50 B50*0 Software—data collection and data processing:
DVSWin v2.18 (control software),
DVS Standard Analysis Suite v4.3 (analysis software).]

Procedure for HPAEC Analysis

The chemical purity of phosphoesters (including the isomeric purity for geometric isomers) is determined using High Performance Anion-Exchange Chromatography (HPAEC) with suppressed conductivity detection. The HPAEC device comprises a DIONEX DX600 system (DIONEX Corporation, Sunnyvale Calif., USA) connected to computer loaded with DIONEX Chromeleon® chromatography software. A DIONEX CD25 conductivity detector is used with an anion self regenerating suppressor (ASRS®-ultra II-4 mm), which is set to either auto-suppression mode or external water mode. The HPAEC column used is a DIONEX Ion Pac® AS11 column (4×250 mm) equipped with an AG11 guard column (4×50 mm). In this procedure, phosphoesters are eluted (as anionic form) from the anion exchange column with a sodium or potassium hydroxide step gradient.

Procedure for the Resolution of the Crystal Structure

The crystals were obtained by a slow crystallisation in a saturated gel of tetramethylsiloxane (TMOS) as detailed here. A saturated solution of CHDMAPP-Na$_2$,1H$_2$O at 28° C. in H$_2$O-EtOH (40-60, wt %) was filtered and placed at 50° C. with 5% (vol). of TMOS. After 24 h in the oven (50° C.), the gel was set. Then, the tube was placed at 28° C., after seeding at the top by fine compound A, a linear cooling was applied from 28° C. to 22° C. in 50 h.

The crystal structure of CHDMAPP-Na$_2$,1H$_2$O has been determined from single crystal X-Ray diffraction. The chosen crystal was stuck on a glass fiber and mounted on the full three-circle goniometer of a Bruker SMART APEX diffractometer with a CCD area detector. Three sets of exposures (a total of 1800 frames) were recorded, corresponding to three Ω scans (steps of 0.3°), for three different values of φ. Crystal data and details of data collection are given in table 5 and 6.

The cell parameters and the orientation matrix of the crystal were determined by using SMART Software. Data integration and global cell refinement were performed with SAINT Software. Intensities were corrected for Lorentz, polarization, decay and absorption effects (SAINT and SAD-ABS Software) and reduced to $F_O^2$. The program package WinGX was used for space group determination, structure solution and refinement.

Data processing involved determining the non standard space group $P2_1/a$ (n° 14) from systematic extinctions and relative $F_O^2$ of equivalent reflections. After a matrix transformation the standard space group $P2_1/c$ was obtained. The crystal structure was solved by direct methods (SIR 92). Anisotropic displacement parameters were refined for all non-hydrogen atoms. Every hydrogen atom was located from subsequent difference Fourier syntheses and refined isotropically (SHELXL[5]). The final cycle of full-matrix least-square refinement on $F^2$ was based on 2612 observed reflections and 175 variable parameters and converged with unweighted and weighted agreement factors of: R1=0.0358, wR2=0.0879 for [$F^2$>2σ(F)] and R1=0.0411, wR2=0.0909 for all data.

TABLE 6

Acquisition parameters of the X-Ray diffraction analysis on single crystal

| | |
|---|---|
| Temperature/K | RT |
| Radiation | Mo-Kα$_1$ (λ = 0.71073 Å) |
| Monochromator | Graphite |
| Collimator/mm | 0.5 |
| Generator set | 50 kV 40 mA |
| Crystal-detector distance/mm | 60 |
| Detector 2θ angle/° | −28 |
| ω oscillations/° | −0.3 |
| ω scan 1 | χ = 54.7°, φ = 0°, −28° ≤ ω ≤ −208° |
| ω scan 2 | χ = 54.7°, φ = 120°, −28° ≤ ω ≤ −208° |
| ω scan 3 | χ = 54.7°, φ = 240°, −28° ≤ ω ≤ −208° |
| Time exposure/s | 5 |

Example 1

Preparation of CHDMAPP

Preparation of (E)-4-chloro-2-methylbut-2-en-1-ol

Following the method of Hecht et al. (Hecht et al., *Tetrahedron Letters*, 43 (2002) 8929-8933) commercially available 2-methyl-2-vinyloxirane is converted into (E)-4-chloro-2-methylbut-2-en-1-ol by treatment with TiCl4 at −80° C. to −90° C.

Preparation of (E)-4-chloro-2-methylbut-2-en-1-(pyranyl-2'-oxy)

Following the method of Miyashita et al. (Miyashita et al., *J. Org. Chem.* 42 (1977) 3772-3774), the allylic alcohol is converted into a protected form by reaction of (E)-4-chloro-2-methylbut-2-en-1-ol with Dihydropyrane (DHP) in the presence of Pyridinium p-Toluenesulfonate (PPTs).

Preparation of methyl methylphosphonomorpholidate

Following the method of Valentijn et al. for the preparation of Farnesyl Pyrophosphate analogues (Valentijn et al., *Synlett* (1991) 663-664), the phosphonylating agent is prepared by treatment of commercially available methylphosphonic dichloride with morpholine and methanol.

Preparation of Intermediate

Following the method of Valentijn et al. (Valentijn et al., *Synlett* (1991) 663-664), intermediate is prepared by reaction of (E)-4-chloro-2-methylbut-2-en-1-(pyranyl-2'-oxy) with methyl lithiomethylphosphonomorpholidate obtained in situ from the phosphonylating agent methyl methylphosphonomorpholidate.

Preparation of (2E)-1-hydroxy-2-methylpent-2-enyl-pyrophosphonate (CHDMAPP)

A crude solution of C-HDMAPP is obtained in a 3 step procedure:
1. demethylation of intermediate by treatment with tetra-n-butylammonium hydroxide in methanol as reported by Phan and Poulter (J. Org. Chem. (2001), 66, 6705-6710),
2. coupling with phosphoric acid following the procedure of Valentijn et al. (Valentijn et al., *Synlett* (1991) 663-664), and
3. deprotection of the pyranyl-2'-oxy group by subsequent treatment of the pyrophosphonate ester with chlorhydric acid at pH 1-2 to yield a crude solution of CHDMAPP.

Example 2

Preparation of the crystalline monohydrate of (2E)-1-hydroxy-2-methylpent-2-enyl-pyrophosphonate disodium (CHDMAPP-Na$_2$,1H$_2$O)

50 g of CHDMAPP disodium (purity 98.49%) have been diluted in 150.3 g of purified and deionized water (R=18.5 MΩ). The solution has been introduced slowly in a double-shell reactor (internal diameter 100 mm). Temperature was carefully controlled and maintained at 20° C. using a cryo-thermostat device (Huber® polystat CC240). The mixture has been stirred using a glass stirrer (200-300 rpm-diameter 70 mm, rotation speed 250 rpm). 279 g of ethanol has been added drop wise to the medium during 60 minutes, until the intermediate composition of the medium was 35/65; water/ethanol. A white suspension was obtained and the medium has been gently stirred for 60 additional minutes before another ethanol addition. 1071 g of ethanol have been added drop wise during 4 hours, leading to a final medium composition of 90/10; water/ethanol. The obtained solid has been filtrated on a fritted glass (porosity 3, diameter 190 mm) and dried under a constant flux of nitrogen until a constant mass has been observed. The crystallized CHDMAPP-Na$_2$,1H$_2$O crystalline compound has been obtained as a white solid with an overall yield of 96.42% (48.21 g).

Example 3

ICH stability testing of the API crystalline CHDMAPP-Na$_2$,1H$_2$O (chemical purity)

Stability tests of CHDMAPP-Na$_2$,1H$_2$O have been conducted according to ICH guideline Q7a, Section 19.11, under various storage conditions: 5° C., and 25° C./60% RH, both in closed glass vials. Purity has been assessed at regular time intervals (t0, 1, 3, 6 and 9 months) by HPAEC using a Dionex Ion Pac AS11, 4.0×250 mm column and a Dionex Ion Pac AG11, 4.0×250 mm pre-column and by eluting with a gradient of water and NaOH solution.

| Storage conditions | t 0 | 1 month | 3 months | 6 months | 9 months |
|---|---|---|---|---|---|
| 5° C. | 99.3 | 99.1 | 99.2 | 98.8 | 98.9 |
| 25°C./60% R.H. | 99.3 | 99.2 | 99.1 | 98.7 | 98.9 |

Example 4

Preparation of the crystalline anhydrous form of (2E)-1-hydroxy-2-methylpent-2-enyl-pyrophosphonate disodium (CHDMAPP-Na$_2$,0H$_2$O)

1.067 g of CHDMAPP-Na$_2$ (purity 98.08%) were added in 10.064 g of pure ethanol. The final composition in solute/solvent was 9.6/90.4 respectively. The suspension was stored in a jacket carefully controlled and maintained at 20° C. using a cryo-thermostat device (Huber® polystat CC240). The mixture was stirred for 24 hours using a magnetic stirrer (rotation speed 300 rpm). The obtained solid was filtrated on a fritted glass (porosity 3) and dried under a constant flux of nitrogen until a constant mass was observed. The CHDMAPP-Na$_2$,0H$_2$O crystalline compound was obtained as a white solid with an overall yield of 99%.

The invention claimed is:

1. A crystalline (2E)-1-hydroxy-2-methylpent-2-enyl-pyrophosphonate disodium composition (CHDMAPP-Na$_2$).

2. The composition of claim 1, crystallized as a monohydrate polymorph (CHDMAPP-Na$_2$,1H$_2$O).

3. The composition of claim 1, crystallized as an anhydrous polymorph (CHDMAPP-Na$_2$,0H$_2$O).

4. The composition of claim 2, wherein said composition is characterized by an XRPD pattern comprising at least one of the peaks (2-theta angles) of the phases (A) to (T), said peaks of phases (A) to (I) being selected from the group consisting of the peaks at about:
   (A) 7.25;
   (B) 10.81;
   (C) 12.32;
   (D) 14.04;
   (E) 14.54;
   (F) 16.06;
   (G) 16.61;
   (H) 17.61;
   (I) 18.68;
   (J) 19.44;
   (K) 19.80;
   (L) 20.13;
   (M) 21.34;
   (N) 21.84;
   (O) 23.36;
   (P) 24.52;
   (Q) 25.26;
   (R) 25.98;
   (S) 26.84; and
   (T) 27.16.

5. The composition of claim 4, wherein said phase is characterized by an XRPD pattern comprising at least four, at least five, at least six peaks expressed in terms of theta-2 angles of a phase selected from the group consisting of (A) through (T).

6. The composition of claim 2, wherein said composition is characterized in that the crystalline form is stable until 115° C.±2° C.

7. The composition of claim 2, wherein said composition is characterized by a DSC pattern comprising an endothermic peak having an onset temperature of about 115° C.±2"C and a maximum peak temperature of about 130° C.±2° C.

8. The composition of claim 2, wherein said composition is characterized by a DVS pattern wherein no substantial weight gain occurs before about 80%±2% RH.

9. The composition of claim 2, wherein said composition is characterized by at least one of the following crystallographic parameters:

| | |
|---|---|
| Chemical formula | Na$_2$[HO—CH$_2$—C(CH$_3$)=CH—(CH$_2$)$_2$—PO$_2$—O—PO$_3$H],H$_2$O |
| Molar mass/g · mol$^{-1}$ | 322.09 |
| Crystalline system | Monoclinic |
| Space group | P 2$_1$/c (n° 14) |
| Z | 4 |
| Z' (asymmetric unit) | 1 |
| a/Å | 12.201(1) |
| b/Å | 11.03(1) |
| c/Å | 9.495(1) |
| β (°) | 92.928(2) |
| V/Å$^3$ | 1276.1(3) |
| d$_{calc}$/g · cm$^{-3}$ | 1.677 |
| Temperature/K | RT. |

10. The composition of claim 3, wherein said composition is characterized by an XRPD pattern comprising at least one of the peaks (2-theta angles) of the phases (A) to (T), said peaks of phases (A) to (T) being selected from the group consisting of the peaks at about:
   (A) 6.83;
   (B) 10.49;
   (C) 15.04;
   (D) 16.88;
   (E) 17.99;
   (F) 18.33;
   (G) 19.12;
   (H) 19.73;
   (I) 19.97;
   (J) 20.45;
   (K) 20.86;
   (L) 21.10;
   (M) 22.67;
   (N) 24.18;
   (O) 25.95;
   (P) 26.84;
   (Q) 27.18;
   (R) 27.36;
   (S) 28.90; and
   (T) 29.18.

11. The composition of claim 10, wherein said phase is characterized by an XRPD pattern comprising at least four, at least five, at least six peaks expressed in terms of theta-2 angles of a phase selected from the group consisting of (A) through (T).

12. The composition of claim 3, wherein said composition is characterized by at least one of the following crystallographic parameters:

| | |
|---|---|
| Chemical formula | Na$_2$[HO—CH$_2$—C(CH$_3$)=CH—(CH$_2$)$_2$—PO$_2$—O—PO$_3$H] |
| Molar mass/g·mol$^{-1}$ | 304.07 |
| Crystalline system | Orthorhombic |
| Space group | P n a 2$_1$ (n° 33) |
| Z | 4 |
| Z' | 1 |
| a/Å | 9.852(5) |
| b/Å | 26.049(5) |
| c/Å | 8.901(5) |
| V/Å$^3$ | 2284.3(2) |
| d$_{calc}$/g·cm$^{-3}$ | 1.768 |
| Temperature/K | RT. |

13. The composition of claim 1, wherein said composition is stable for a period of time of at least 3 months at ambient temperature.

14. A pharmaceutical composition comprising the composition of claim 1.

15. A process to obtain a solid crystalline (2E)-1-hydroxy-2-methylpent-2-enyl-pyrophosphonate disodium composition, comprising:

a) diluting (2E)-1-hydroxy-2-methylpent-2-enyl-pyrophosphonate disodium in water,
b) adding an organic solvent until the formation of crystals,
c) isolating the crystals, and
d) drying the crystallized (2E)-1-hydroxy-2-methylpent-2-enyl-pyrophosphonate disodium monohydrate.

16. A process to further purify (2E)-1-hydroxy-2-methylpent-2-enyl-pyrophosphonate disodium monohydrate, said method comprising the steps of:

(a) crystallizing (2E)-1-hydroxy-2-methylpent-2-enyl-pyrophosphonate disodium monohydrate according to the process of claim 15; and
(b) recrystallizing the (2E)-1-hydroxy-2-methylpent-2-enyl-pyrophosphonate disodium monohydrate to obtain a substantially or essentially pure (2E)-1-hydroxy-2-methylpent-2-enyl-pyrophosphonate disodium monohydrate or (2E)-1-hydroxy-2-methylpent-2-enyl-pyrophosphonate disodium monohydrate composition.

17. A substantially pure (2E)-1-hydroxy-2-methylpent-2-enyl-pyrophosphonate disodium monohydrate (CHDMAPP-Na$_2$, 1H$_2$O) composition.

* * * * *

UNITED STATES PATENT AND TRADEMARK OFFICE
CERTIFICATE OF CORRECTION

PATENT NO. : 8,735,624 B2
APPLICATION NO. : 13/063248
DATED : May 27, 2014
INVENTOR(S) : Guillaume Descamps et al.

It is certified that error appears in the above-identified patent and that said Letters Patent is hereby corrected as shown below:

In the Specification,

Column 1,
Line 45, "activate γδ T cells" should read --activate γδ T cells--.

Column 2,
Line 5, "development have shown" should read --developments have shown--.

Column 6,
Line 12, "in represented" should read --is represented--.
Line 38, "$Na_2$-[$HO-CH_2-C(CH_3)=CH-(CH_2)_2-PO_2-O-PO_3H$]" should read
--$Na_2$[$HO-CH_2-C(CH_3)=CH-(CH_2)_2-PO_2-Q-PO_3H$]--.
Line 47, "$CHMDAPP-Na_2$," should read --$CHDMAPP-Na_2$,--.

Column 13,
Lines 6-7, "compounds begins" should read --compound begins--.
Line 17, "peaks at 2θ" should read --peaks at 2θ--.

Column 14,
Line 66, "does not exhibits" should read --does not exhibit--.

Column 15,
Line 2, "is done is a precipitated manner" should read
--is done in a precipitated manner.--.
Line 12, "in on organic" should read --in an organic--.

Column 18,
Line 17, "Systems)=" should read --Systems--.
Line 67, "three Ω" should read --three ω--.

Signed and Sealed this
Tenth Day of February, 2015

Michelle K. Lee
*Deputy Director of the United States Patent and Trademark Office*

CERTIFICATE OF CORRECTION (continued)
U.S. Pat. No. 8,735,624 B2

Column 19,
Line 23, "[$F^2>2\sigma(F)$]" should read --[$F^2>2\sigma(F^2)$]--.

In the Claims,

Column 21,
Line 42, "(A) to (I) being" should read --(A) to (T) being--.

Column 22,
Line 6, "± 2"C and" should read --± 2°C and--.

UNITED STATES PATENT AND TRADEMARK OFFICE
CERTIFICATE OF CORRECTION

PATENT NO. : 8,735,624 B2
APPLICATION NO. : 13/063248
DATED : May 27, 2014
INVENTOR(S) : Guillaume Descamps et al.

It is certified that error appears in the above-identified patent and that said Letters Patent is hereby corrected as shown below:

In the Specification,

Column 1,
Line 45, "activate 76 T cells" should read --activate $\gamma\delta$ T cells--.

Column 2,
Line 5, "development have shown" should read --developments have shown--.

Column 6,
Line 12, "in represented" should read --is represented--.
Line 38, "$Na_2$-[HO-$CH_2$-C($CH_3$)=CH-($CH_2$)$_2$-$PO_2$-O-$PO_3$H" should read
--$Na_2$[HO-$CH_2$-C($CH_3$)=CH-($CH_2$)$_2$-$PO_2$-O-$PO_3$H--.
Line 47, "CHMDAPP-$Na_2$," should read --CHDMAPP-$Na_2$,--.

Column 13,
Lines 6-7, "compounds begins" should read --compound begins--.
Line 17, "peaks at 28" should read --peaks at $2\theta$--.

Column 14,
Line 66, "does not exhibits" should read --does not exhibit--.

Column 15,
Line 2, "is done is a precipitated manner" should read --is done in a precipitated manner.--.
Line 12, "in on organic" should read --in an organic--.

This certificate supersedes the Certificate of Correction issued February 10, 2015.

Signed and Sealed this
Twenty-fifth Day of August, 2015

Michelle K. Lee
*Director of the United States Patent and Trademark Office*

Column 18,
Line 17, "Systems)=" should read --Systems--.
Line 67, "three Ω" should read --three ω--.

Column 19,
Line 23, "[$F^2$>2σ(F)]" should read --[$F^2$>2σ($F^2$)]--.

In the Claims,

Column 21,
Line 42, "(A) to (I) being" should read --(A) to (T) being--.

Column 22,
Line 6, "± 2"C and" should read --± 2°C and--.